(12) United States Patent
Erman

(10) Patent No.: US 10,188,346 B2
(45) Date of Patent: *Jan. 29, 2019

(54) CUBITAL TUNNEL INFOMATIC MONITOR

(71) Applicant: Focal Wellness, Inc., Carlsbad, CA (US)

(72) Inventor: Randal Erman, San Marcos, CA (US)

(73) Assignee: Focal Wellness, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,420

(22) Filed: Nov. 2, 2017

(65) Prior Publication Data

US 2018/0116587 A1 May 3, 2018

Related U.S. Application Data

(63) Continuation-in-part of application No. 15/479,386, filed on Apr. 5, 2017, now Pat. No. 9,808,208.

(60) Provisional application No. 62/434,412, filed on Dec. 15, 2016, provisional application No. 62/413,967, filed on Oct. 27, 2016.

(51) Int. Cl.
*A61B 5/00* (2006.01)
*A61B 5/11* (2006.01)

(52) U.S. Cl.
CPC .......... *A61B 5/486* (2013.01); *A61B 5/1114* (2013.01); *A61B 5/458* (2013.01); *A61B 5/459* (2013.01); *A61B 5/6824* (2013.01); *A61B 5/6825* (2013.01); *A61B 5/7282* (2013.01); *A61B 5/746* (2013.01); *A61B 5/7445* (2013.01); *A61B 5/7455* (2013.01); *A61B 2562/0219* (2013.01); *A61B 2562/0223* (2013.01)

(58) Field of Classification Search
CPC ....... A61B 5/486; A61B 5/746; A61B 5/1116; A61B 5/6806; A61B 5/0488; A61B 5/4836; A61B 2562/164; A61B 5/6824; A61B 2562/0219; A61B 5/7455
USPC .................................................. 340/539.12
See application file for complete search history.

(56) References Cited

U.S. PATENT DOCUMENTS

| | | |
|---|---|---|
| 4,774,966 A | 10/1988 | Lemmen |
| 4,850,341 A | 7/1989 | Fabry et al. |
| 5,031,640 A | 7/1991 | Spitzer |
| 5,501,657 A | 3/1996 | Feero |
| 5,676,476 A | 10/1997 | Uke |
| 5,851,191 A | 12/1998 | Gozani |
| 6,006,751 A | 12/1999 | Spitzer |
| 6,045,517 A | 4/2000 | Williams |
| 6,179,852 B1 | 1/2001 | Strickland et al. |

(Continued)

OTHER PUBLICATIONS

International Search Report for PCT/US2017/058516 dated Feb. 21, 2018.

*Primary Examiner* — John A Tweel, Jr.
(74) *Attorney, Agent, or Firm* — Clause Eight IPS; Michael Catania

(57) ABSTRACT

A device, system and method for monitoring cubital tunnel syndrome ("CuTS"). The device comprises a body configured to be worn by a user, sensors, a processor, a vibration mechanism, and a power source. The sensors monitor a position of the user's hand to prevent CuTS. The processor of the device is configured to determine if the user's hand is in a CuTS position and the processor is configured to generate an alert signal to alert the user to the CuTS position.

12 Claims, 30 Drawing Sheets

(56) References Cited

U.S. PATENT DOCUMENTS

| | | |
|---|---|---|
| 6,510,346 B2 | 1/2003 | Gordon |
| 6,530,893 B1 | 3/2003 | Castelli |
| 6,852,067 B2 | 2/2005 | Limonadi |
| 6,893,396 B2 | 5/2005 | Schulze et al. |
| 7,344,511 B2 | 3/2008 | Porrata et al. |
| 7,364,559 B2 | 4/2008 | Williams |
| 7,834,851 B1 | 11/2010 | Fidali et al. |
| 7,942,918 B2 | 5/2011 | Herzberg et al. |
| 9,223,956 B2 | 12/2015 | Hong et al. |
| 9,387,109 B2 | 7/2016 | Keoshian et al. |
| 9,808,208 B1 * | 11/2017 | Erman .................. A61B 5/746 |
| 2002/0140674 A1 | 10/2002 | Okuno et al. |
| 2006/0004302 A1 | 1/2006 | Tuckett et al. |
| 2007/0156158 A1 | 7/2007 | Herzberg et al. |
| 2008/0181917 A1 | 7/2008 | Pappagallo et al. |
| 2008/0204225 A1 | 8/2008 | Kitchen |
| 2009/0062707 A1 | 3/2009 | Busuttil |
| 2009/0143704 A1 | 6/2009 | Bonneau et al. |
| 2011/0033830 A1 | 2/2011 | Cherian |
| 2011/0208100 A1 | 8/2011 | Eck et al. |
| 2011/0230805 A1 | 9/2011 | Oron |
| 2012/0317693 A1 | 12/2012 | Hatz |
| 2014/0236059 A1 | 8/2014 | Son |
| 2014/0296760 A1 | 10/2014 | Keoshian et al. |
| 2014/0343473 A1 | 11/2014 | Hoffman |
| 2015/0306373 A1 | 10/2015 | Bouton et al. |
| 2016/0015280 A1 | 1/2016 | Hyde et al. |
| 2016/0296406 A1 | 10/2016 | Heyl |
| 2017/0156662 A1 | 6/2017 | Goodall et al. |
| 2017/0164876 A1 | 6/2017 | Hyde et al. |

* cited by examiner

CUBITAL TUNNEL INFOMATIC MONITOR

CROSS REFERENCES TO RELATED APPLICATIONS

The Present application is a continuation-in-part application of U.S. patent application Ser. No. 15/479,386, filed on Apr. 5, 2017, which claims priority to U.S. Provisional Patent Application No. 62/413,967, filed on Oct. 27, 2016, and U.S. Provisional Patent Application No. 62/434,412, filed Dec. 15, 2016, which are all hereby incorporated by reference in their entireties.

STATEMENT REGARDING FEDERALLY SPONSORED RESEARCH OR DEVELOPMENT

Not Applicable

BACKGROUND OF THE INVENTION

Field of the Invention

The present invention generally relates to devices to prevent and recover form carpal tunnel syndrome.

Description of the Related Art

Carpal Tunnel Syndrome (CTS) accounts for nearly 2 billion dollars in estimated care cost within the United States. With that staggering cost in mind new and innovative ways to prevent CTS can yield huge gains for employers while sparing individuals the pain. Sadly the current state of art for CTS is very rudimentary. Doctors inform people that they most likely have CTS and prescribe them anti-inflammatories and then ask them to buy a rigid brace. The normal amount of time lost to CTS is 27 days. Workplaces are then adjusted to help prevent further injury at the expense to the employer. The employer's cost doesn't stop there because statistically people who develop CTS on a certain job leave within 18 months for a new job. Instead of looking at the problem after the fact our technology solution provides a way to quantify, monitor and categorize motions, and provide feedback tools to individuals as well as supervisors to help prevent CTS.

BRIEF SUMMARY OF THE INVENTION

One aspect of the present invention is a device for monitoring carpal tunnel syndrome ("CTS"). The device comprises a body configured to be worn by a user, sensors, a processor, a vibration mechanism, and a power source. The sensors monitor a position of the user's hand to prevent CTS. The processor of the device is configured to determine if the user's hand is in a CTS position and the processor is configured to generate an alert signal to alert the user to the CTS position.

Another aspect of the present invention is a method for monitoring carpal tunnel syndrome ("CTS"). The method includes monitoring a position of the user's hand to prevent CTS using a plurality of sensors on an article. The method also includes determining that the user's hand is in a CTS position from a signal from the plurality of sensors. The method also includes generating an alert signal to alert the user to the CTS position.

Yet another aspect of the present invention is an article for monitoring carpal tunnel syndrome ("CTS"). The article comprises a body configured to be worn by a user, a plurality of sensors, a processor, a vibration mechanism, and a power source. The plurality of sensors monitors a position of the user's hand to prevent CTS. The processor of the article is configured to determine if the user's hand is in a CTS position and the processor is configured to generate an alert signal to alert the user to the CTS position.

The sensors are preferably either a single or multiple piezoelectric sensors. In an alternative embodiment, the sensors are inertia measurement unit (IMU) sensors. In yet an alternative embodiment, the sensors are a combination of IMU and piezoelectric sensors. In various embodiments, each of the sensors preferably has an LED for indication of proper hand position.

In one embodiment, the article is a watch, and the plurality of sensors comprises an IMU sensor. In another embodiment, the article is a glove or fingerless sleeve.

In one embodiment, the alert signal is an audio alert. In another embodiment, the alert signal is a visual alert.

In one embodiment, the alert is a vibration mechanism vibrating for indication of a proper hand position.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
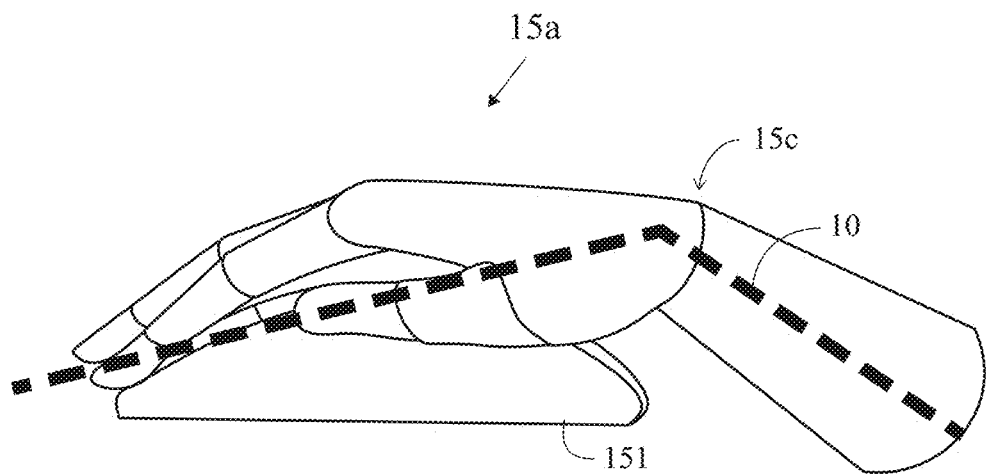
FIG. 1 is an illustration of down-hand carpal use of a mouse by a user.

The carpal tunnel infomatic monitor (C-TIM) is a state of the art monitor system designed to quantify and monitor wrist position for a user's single wrist or both wrists.

The C-TIM wrist glove/sleeve itself is preferably composed of a flexible material or a rigid material based on consumer preferences.

The C-TIM preferably utilizes both wired and wireless means of communication with a host system to provide data to an application software running on a computing device such as a laptop computer, desktop computer or Smartwatch or mobile device.

In one embodiment, the C-TIM comprises a microprocessor, a vibration mechanism, a wireless chipset such as WiFi, BT, BTLE, UWB or NFC, a plurality of 10 Degree of Freedom (DOF) sensor technology (Gyroscopes), and a battery.

In an alternative embodiment, the C-TIM comprises a microprocessor, a vibration mechanism, a wireless chipset such as WiFi, BT, BTLE, UWB or NFC, a plurality of IMU, and a battery.

The C-TIM alternatively includes a charging circuit depending upon which type of battery technology is incorporated.

The C-TIM alternatively includes include a blood rate monitor.

The C-TIM alternatively includes LEDs to indicate if the wrist is in a proper position.

The C-TIM alternatively includes LEDs to indicate the state of the power circuit and battery power level.

The C-TIM alternatively includes a sound buzzer which is utilized to give additional feedback to users about proper or improper wrist position.

The C-TIM alternatively includes a shaking/motion device to give physical feedback in terms of correct or incorrect wrist position.

C-TIM is preferably configured with any number of IMUs directly integrated onto the same board as the microprocessor, or a subset of IMUs directly integrated onto the same board as the microprocessor and remaining subset connected to that board in some fashion, or all IMUs connected to the microprocessor board in some manner known to those skilled in the pertinent art.

The C-TIM is preferably composed of a microprocessor with embedded wireless technology such as WiFi, BT, BTLE, UWB, or NFC, and the needed sensor technology.

The C-TIM sensor technology preferably includes any combination of the following depending on the information required: zero or more IMUs, zero or more blood rate sensors, zero or more force sensors, zero or more push buttons/switches, and zero or more strain sensors.

The C-TIM wrist monitor system is a novel and innovative solution to carpal tunnel monitoring because of its inclusion of real-time processing of wrist position and alerting a user that the user is stressing his/her wrist in a manner that could lead to CTS.

The C-TIM platform preferably includes a mechanism to store all data to a cloud database for further processing and analytics.

The C-TIM software solution also preferably includes an algorithm to determine words, keystroke pattern mannerisms, mouse movements, and other profile information about the situation that may cause an incorrect wrist position. The algorithm is designed to determine which applications cause injury and that information is then used by the user to help correct hand position, provide feedback to the implementers of the program, and/or provided to researchers. The software algorithm is also utilized to train users to avoid the wrist stress positions.

In one embodiment, the C-TIM system encompasses a software dashboard where an individual's usage records, patterns and information is viewed in more detail. The dashboard is further extended in an enterprise model concept that includes the capability to add and track numerous C-TIM instances and assign them to individuals. This type of application preferably provides feedback of ergonomic improvements to the workplace, and produces the correct wrist position for individuals. Alternatively, the dashboard includes a feature that shows which user of a group is putting the most stress on his/her wrist.

Alternatively, a web portal and/or mobile application are provided by which an ergonomic manager determines which individual has the worst wrist angle.

Alternatively, a web portal and/or mobile application are provided by which an ergonomic manager sorts and filters users' attributes. Such attributes allow for ergonomic managers to test and trial out new workplace equipment and configuration in an attempt to determine what helps cohorts of users the best.

Preferably a C-TIM device is provided to a single individual user, but C-TIM devices may also be provided to departments such that numerous users may checkout and use the C-TIM device on different days. With this embodiment of numerous users of a single C-TIM device, a design that includes disposable inserts placed within the sleeve allows for reusability between users.

In one embodiment, data from sensors is categorized by wrist position.

In another embodiment, data from wrist position and other information such as heart rate information is processed into an actionable advice for the consumer. Such advice may include modifications to the environment in which the computer interaction is occurring, modification to the individual's wrist position, and or advice to get up and walk for five minutes as the person has been typing continuously for fifty-five minutes.

In another embodiment, data from sensors is categorized into wrist position as well as a calculation if that position is "optimal", "borderline", or "bad." The "optimal", "borderline", or "bad" calculation is preferably calibrated for each individual.

The C-TIM software program preferably visually or audibly provides feedback to users when the categorized wrist position is in an "optimal", "borderline" or bad position.

Preferably a web Portal and/or mobile application is provided by which an ergonomic manager views analytics of numerous employees.

The analytics preferably include but are not limited to: right hand, left hand, or both hands, time of use, duration of use, average wrist angle, max wrist angle, time at each given wrist angle, typing time, mouse time, application in use, and RSSI value.

The device preferably uses the sensor data to compute an angle of the user's hand relative to the user's wrist. In one embodiment, the C-TIM device includes an accelerometer and a number of gyros/compass sensors which are used to create pitch and yaw.

Consumers after putting on the C-TIM device and activating it, will need to calibrate the C-TIM device. In the embodiment, where the C-TIM device is operating in stand-alone mode, where it is not connected to a host device via wired or wireless means, the calibration is done by pressing a button on the C-TIM device. The button then sets a base position for the user, and will alert the user when an inappropriate wrist angle has been reached. The alert is done in standalone mode by a vibration, a sound, or a light change.

In the case where the C-TIM device is operating in a connected mode, where the device is communicating with the host, the software may ask if calibration data isn't present for the user to place their wrist in a flat position for some number of seconds. When that timeframe has been reached with a valid calibration measurement (e.g., the user's hand isn't moving erratically) the system stores the calibration for future use. Users are then notified via a notification on the host device when the user's wrist moves into an improper angle.

The angle is calculated by determining a user's calibrated flat value, where both IMU sensors baseline become a plane, and then determining if change in relative slope on the key access has gone past a predetermined threshold where carpal tunnel syndrome may occur. The threshold in the case of the standalone is hardcoded into the system or configured via some mechanism such as button press length or wired configuration. The threshold in the case of the connected C-TIM device is manageable via a control panel, which is accessed on the host device. The control panel allows the user to select a frequency of notification, an amount of time beyond the threshold before a notification should be sent, and an angle of the threshold.

FIG. 1 illustrates a down-hand carpal use of a mouse 151 by a user wherein a user's hand 15a is at a downward angle 10 relative to a user's wrist 15c.

Figure 2:
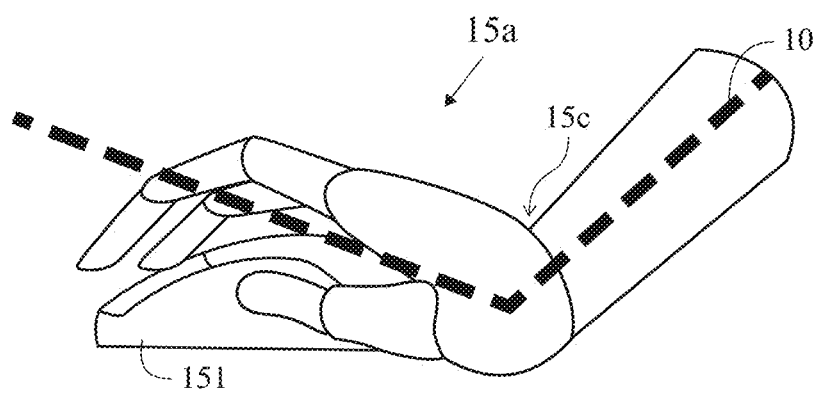
FIG. 2 is an illustration of up-hand carpal of a mouse by a user.

FIG. 2 illustrates an up-hand carpal use of a mouse 151 by a user wherein a user's hand 15a is at an upward angle 10 relative to a user's wrist 15c.

Figure 3:
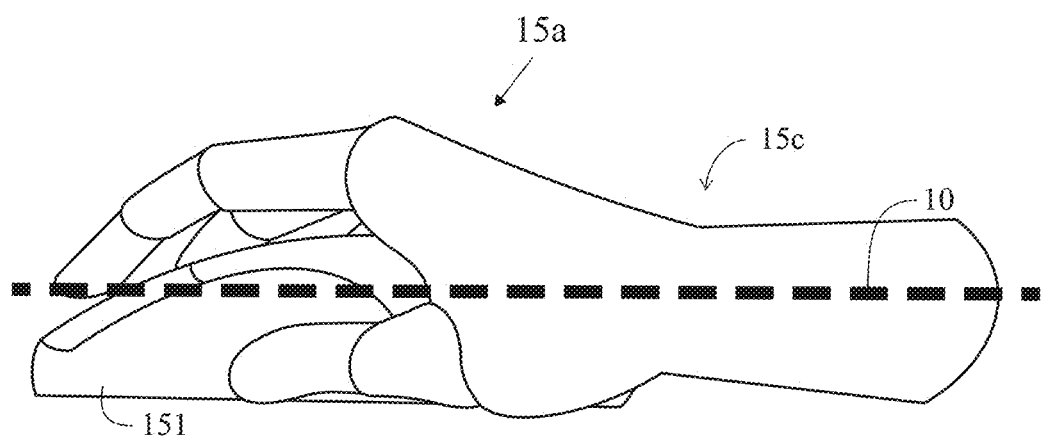
FIG. 3 is an illustration of good carpal use of a mouse by a user.

FIG. 3 illustrates a good carpal use of a mouse 151 by a user wherein the user's hand 15a is at a zero angle 10 relative to the user's wrist 15c.

Figure 4:
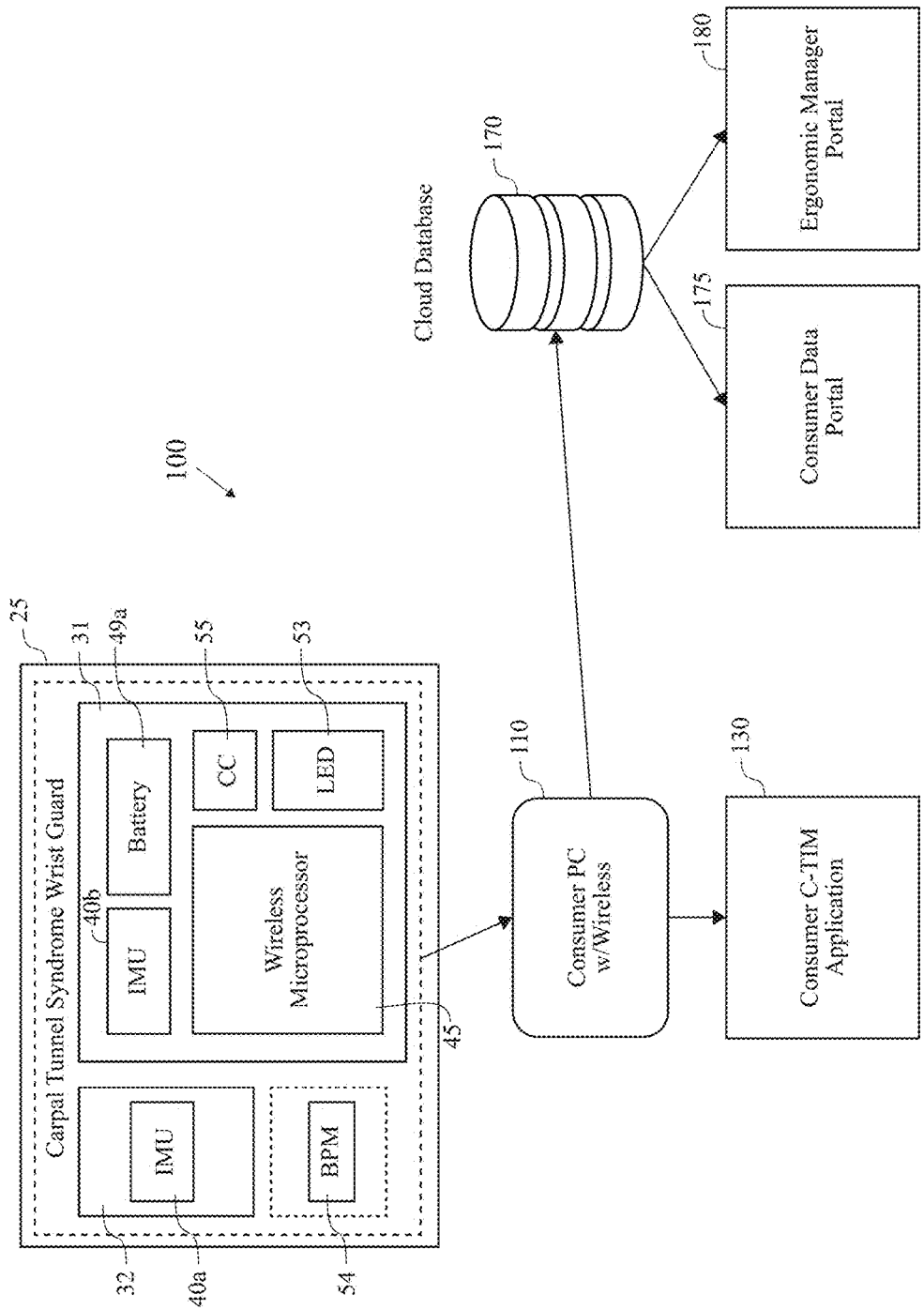
FIG. 4 is a block diagram of a system for monitoring carpal tunnel syndrome.

FIG. 4 is a block diagram of a system 100 for monitoring CTS. The system 100 preferably includes a device 25 worn by a user, a computer 110 running a software application 130 for monitoring CTS, and a cloud database 170 comprising a consumer data portal 175 and an ergonomic manager portal 180. The monitoring device 25 preferably includes a microprocessor with an integrated wireless transceiver, a LED, a battery, a first IMU and a second IMU.

Figure 5:
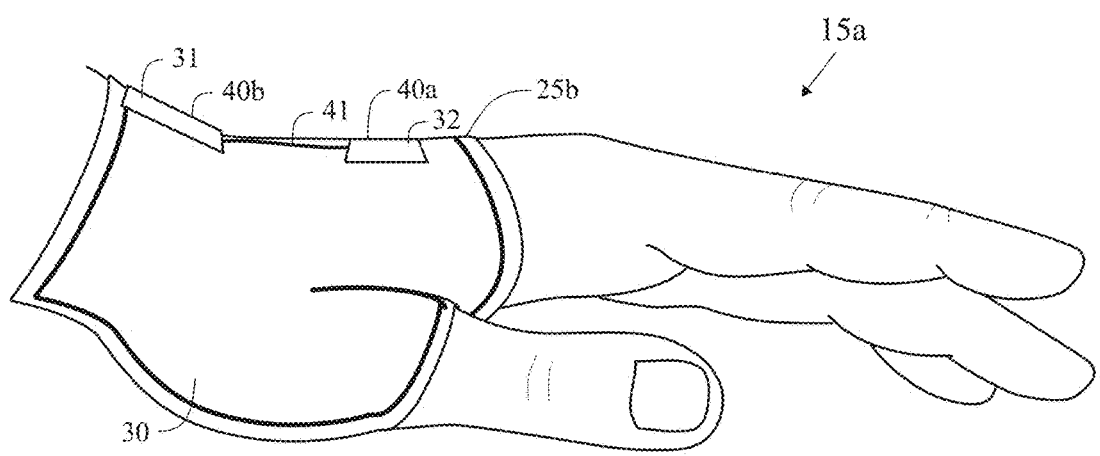
FIG. 5 is an illustration of a device for monitoring carpal tunnel syndrome on a hand of a user.
Figure 6:
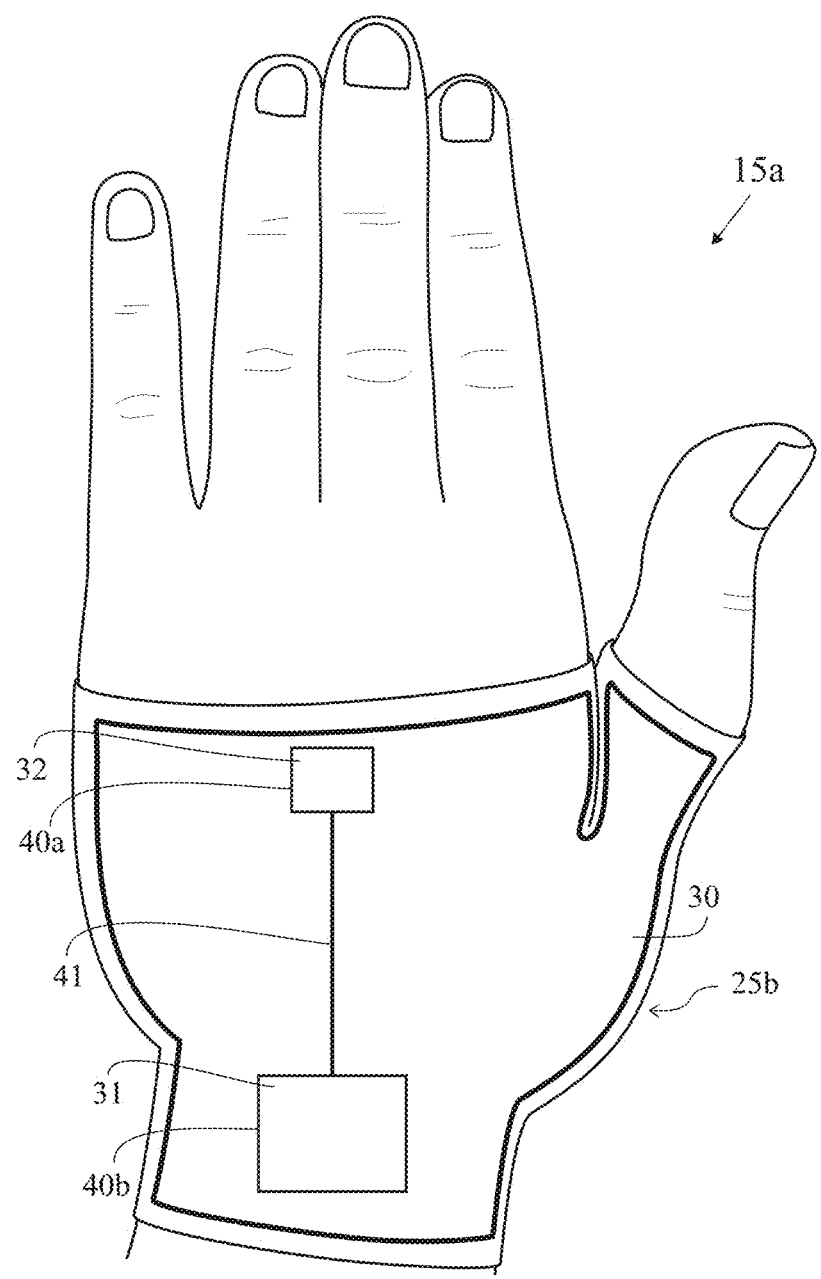
FIG. 6 is an illustration of a device for monitoring carpal tunnel syndrome on a hand of a user.

FIGS. 5 and 6 illustrate a device 25b (a fingerless glove) for monitoring carpal tunnel syndrome on a hand 15a of a user. The device 25b includes a body 30, a first circuit board, a second circuit board 32, a first sensor 40a on the second circuit board 32, a second sensor 40b on the first circuit board 31, and a wire 41 connected between the circuit boards 31 and 32.

Figure 7:
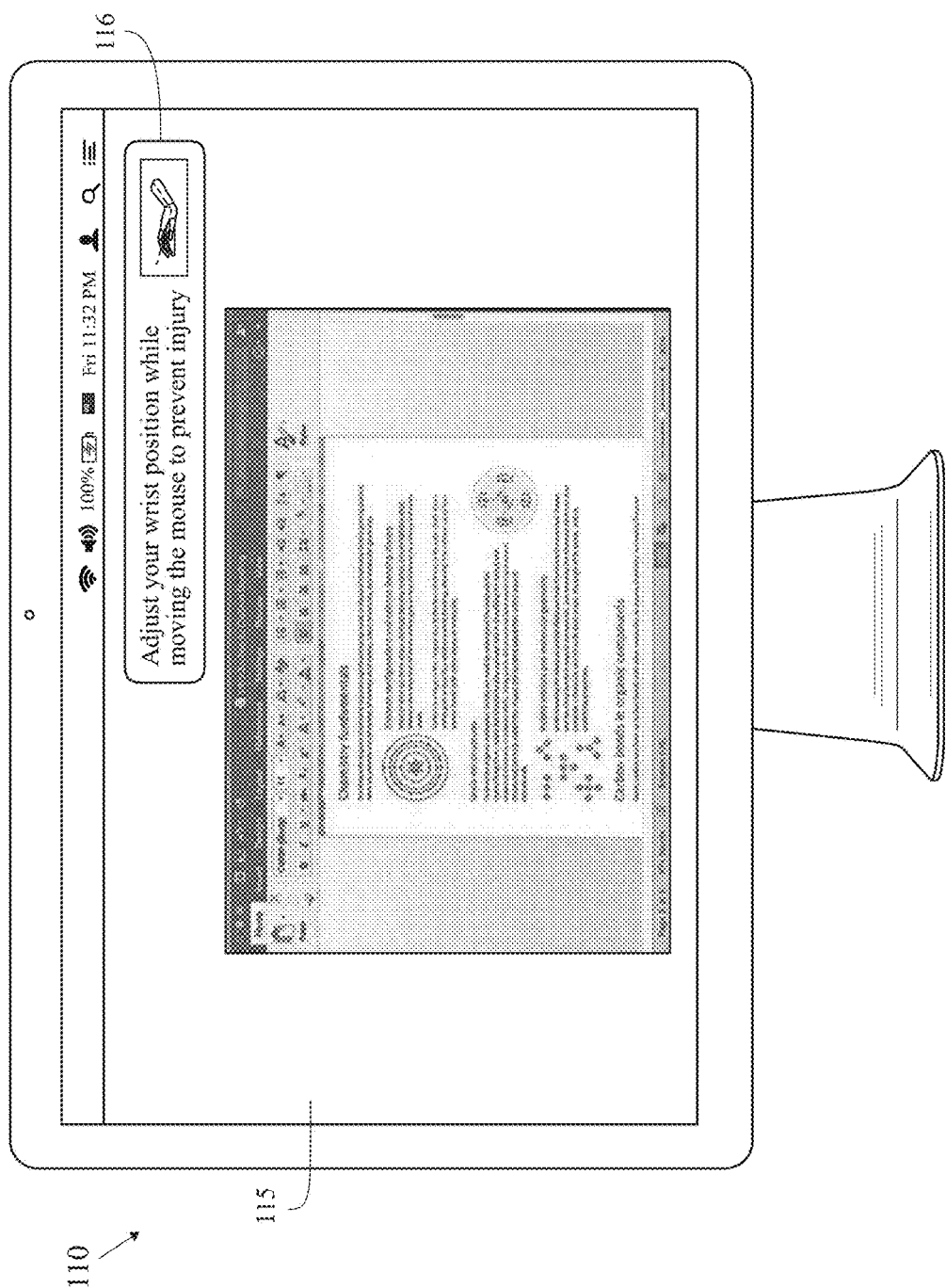
FIG. 7 is an illustration of a display screen for a system for monitoring carpal tunnel syndrome.

FIG. 7 illustrates a computer 110 for a system 100 for monitoring carpal tunnel syndrome. The computer 110 has a display screen 115. A software application running on the computer generates a warning 116 when a user that is wearing a device 25 is in a CTS position when using a mouse or keyboard.

Figure 8:
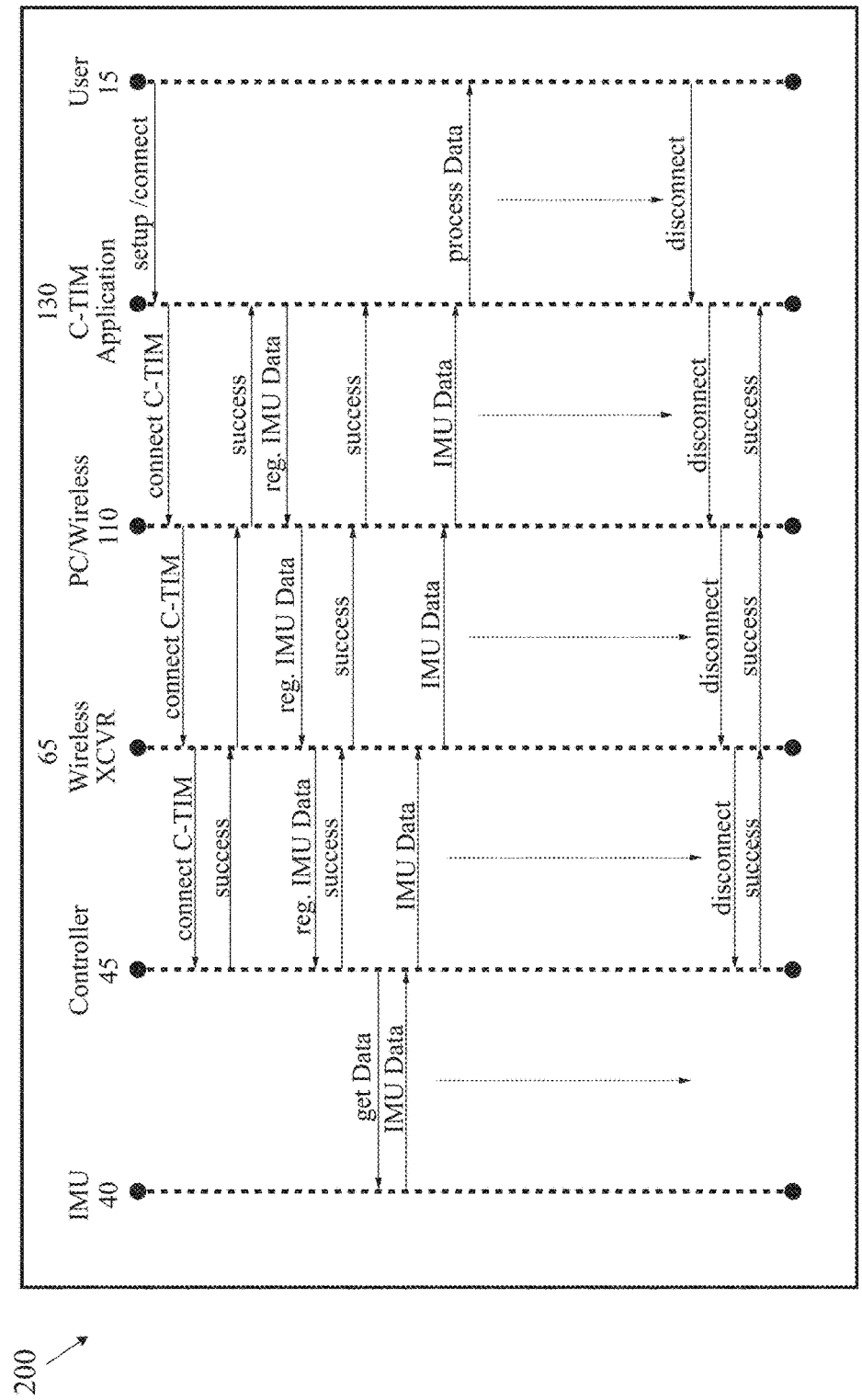
FIG. 8 is a communication sequence diagram for a system for monitoring carpal tunnel syndrome.

FIG. 8 is a communication sequence diagram 200 for a system for monitoring carpal tunnel syndrome. At an initial stage, the user 15 connects to and sets up the software application 130 running on the computer 110. The software application 130, via a wireless transceiver on the computer 110, connects to the controller 45 of the device 25 through a wireless transceiver 65. The controller 45 confirms the set up with the software application 130. The software application 130 registers IMU data with the controller 45. The controller 45 confirms the registration with the software application 130. The controller 45 sends a request for IMU sensor data from the IMU sensor 40. The IMU sensor 40 transmits the IMU data to the software application 130, and the software application 130 processes the IMU data and displays a signal for the user 15. When the user 15 is finished, a disconnect signal is transmitted to the software application 130, which transmits the signal to the controller 45. The controller 45 transmits a success confirmation to the software application 130.

Figure 9:
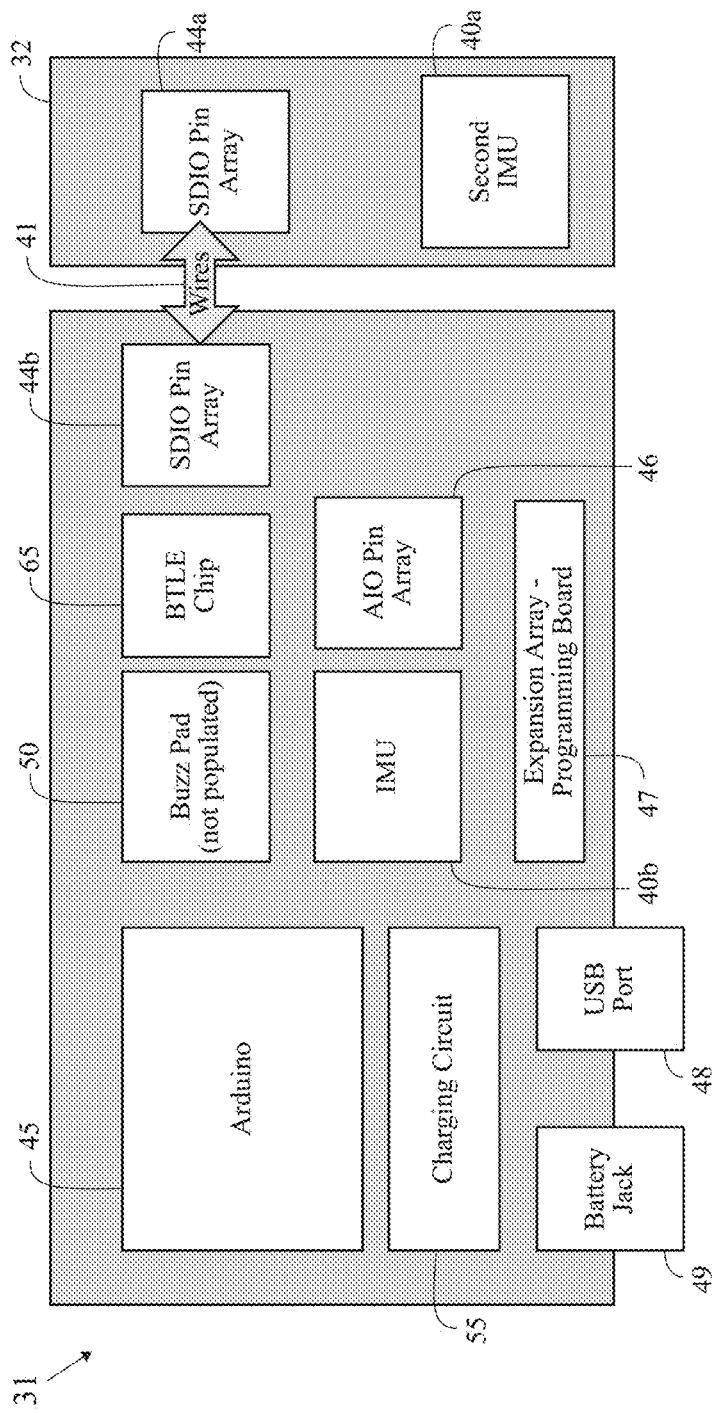
FIG. 9 is block diagram of components for a device of a system for monitoring carpal tunnel syndrome.

FIG. 9 is block diagram of components for a device of a system for monitoring carpal tunnel syndrome. The first circuit board 31 preferably comprises a processor 45, a charging circuit 55, a buzz pad 50, a BLUETOOTH low energy chip 65, SDIO (secure digital input/output) pin array 44b, an AIO (asynchronous input/output) pin array 46, an expansion array programming board 47, a USB port 48, a battery jack 49, and a first sensor (IMU) 40b. The second circuit board 32 preferably includes a SDIO pin array 44a and a second sensor (IMU) 40a.

Figure 9A:
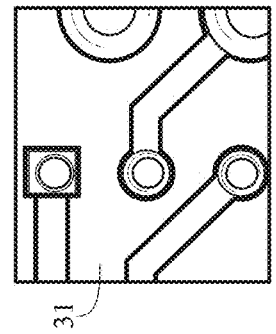
FIG. 9A is an enlarged block diagram of circuitry for a device of a system for monitoring carpal tunnel syndrome.

FIG. 9A is an enlarged view of the first circuit board 31.

Figure 10:
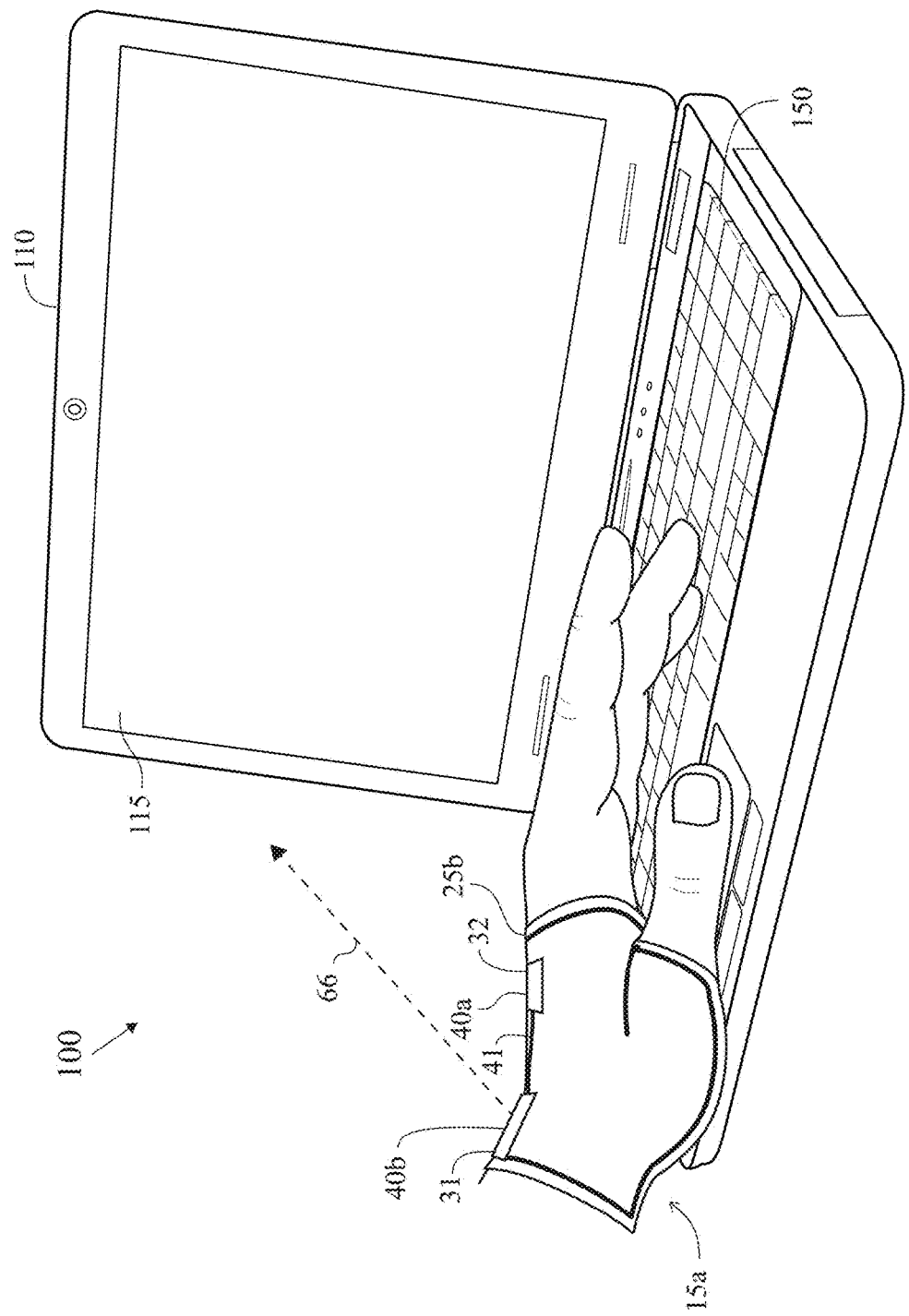
FIG. 10 is an illustration of a user utilizing a system for monitoring carpal tunnel syndrome.

FIG. 10 is an illustration of a user utilizing a system 100 for monitoring carpal tunnel syndrome. The user is a wearing a device 25b (a fingerless glove) on his/her hand 15a while typing on a keyboard 150 of a laptop computer 110. The computer 110 has a display screen 115, and is running a software application for monitoring carpal tunnel syndrome. The device 25b includes a body 30, a first circuit board, a second circuit board 32, a first sensor 40a on the second circuit board 32, a second sensor 40b on the first circuit board 31, and a wire 41 connected between the circuit boards 31 and 32. When the user's hand is in a poor carpal position (in this example, down hand carpal), a signal 66 is sent from the wireless transceiver of the first circuit board 31 to a wireless transceiver of the computer 110. The signal 66 is a communication that the user is in a poor carpal position. The software application running on the computer 110 receives the communication and will generate a warning (e.g., a pop-up message) of the poor carpal position.

Figure 11:
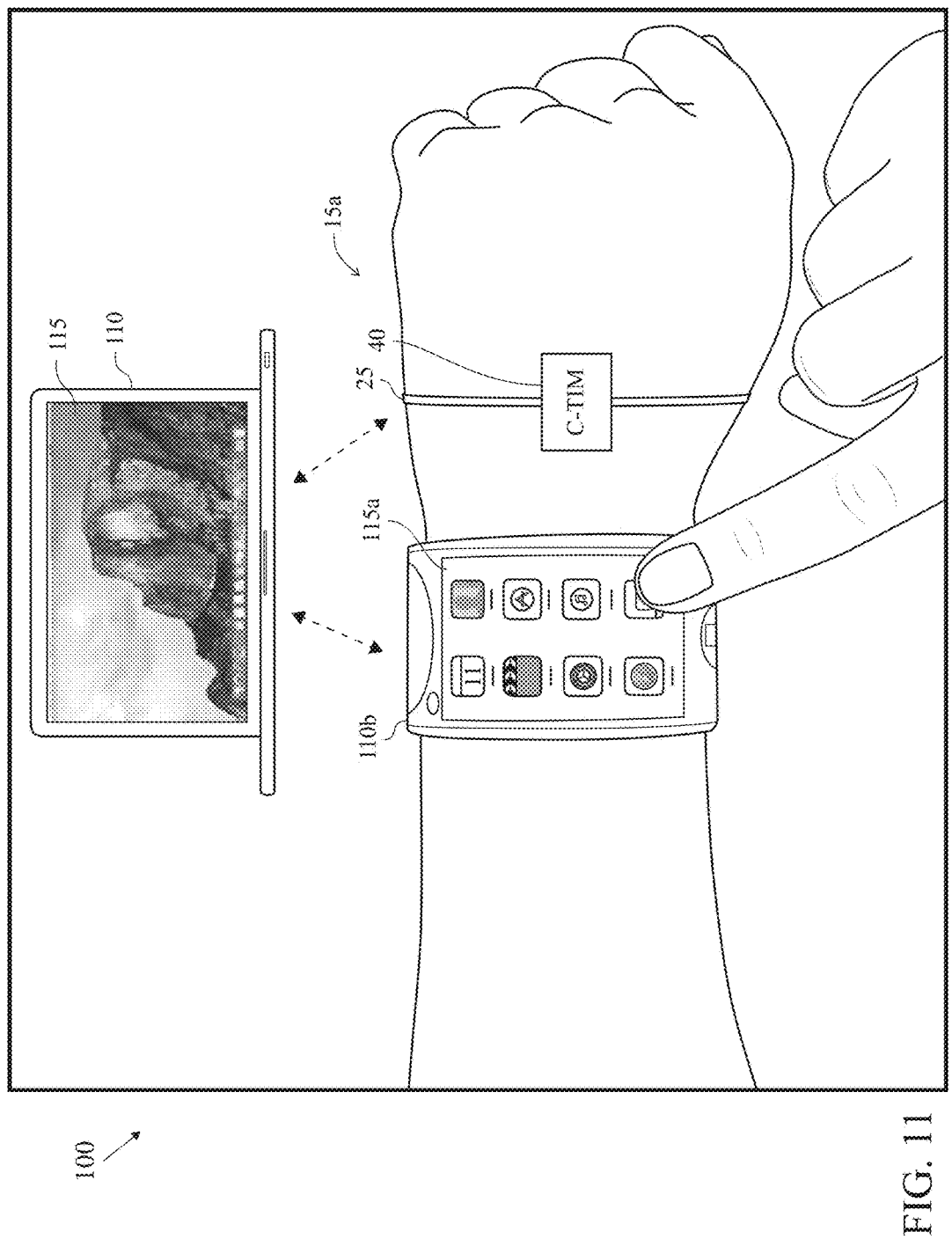
FIG. 11 is an alternative embodiment of a system for monitoring carpal tunnel syndrome.

FIG. 11 is an alternative embodiment of a system 100 for monitoring carpal tunnel syndrome. In this embodiment, a smartwatch 110b is utilized with a device 25 comprising a sensor 40. A sensor in the smartwatch 110b is utilized in conjunction with the sensor 40 of the device 25 to determine an improper hand position for a user. Both the device 25 and the smartwatch 110b are capable of transmitting wireless signals to the computer 110.

Figure 12:
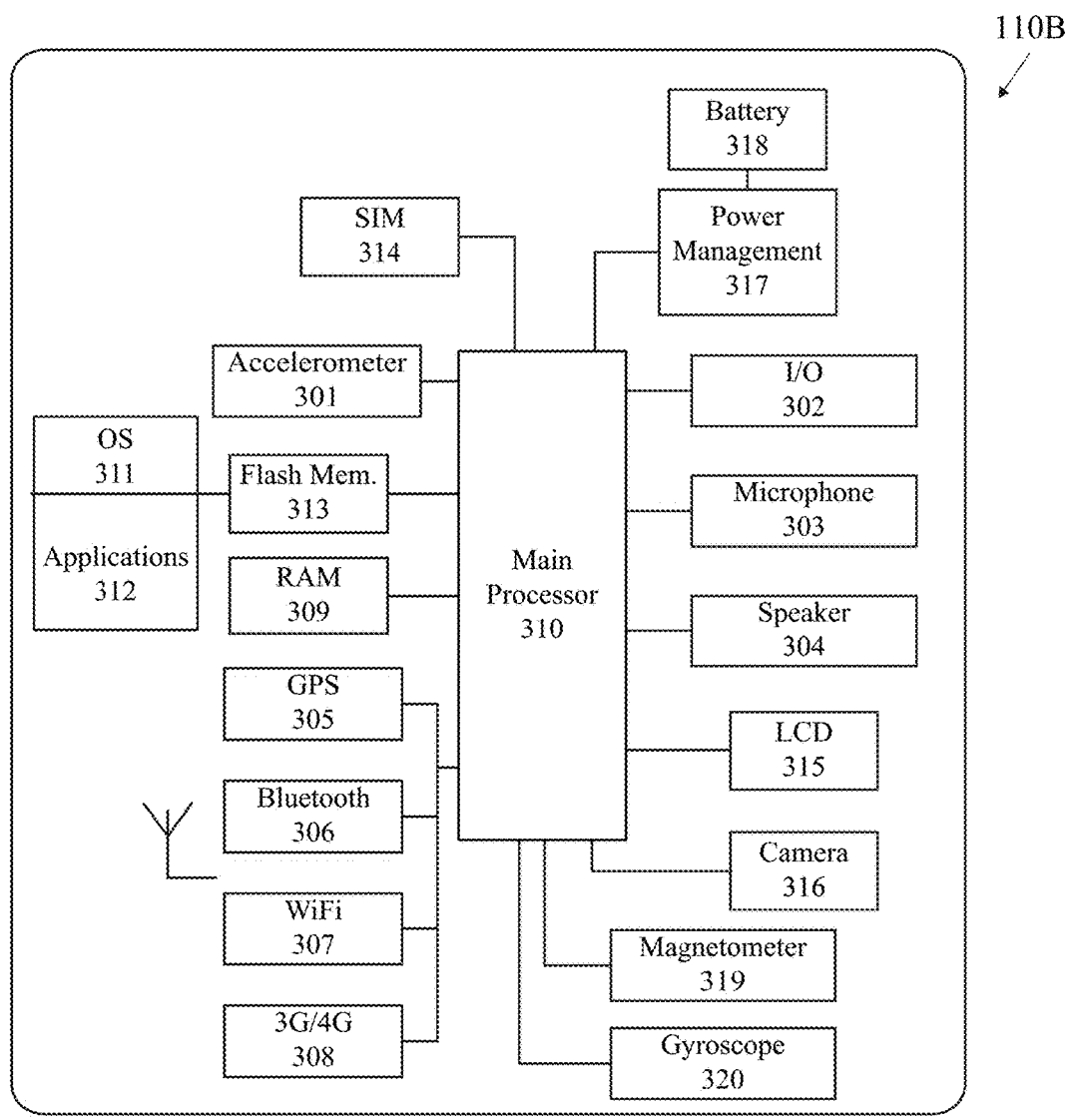
FIG. 12 is a block diagram of a mobile device utilized with a system for monitoring carpal tunnel syndrome.

FIG. 12 is a block diagram of a mobile device 110b utilized with a system 100 for monitoring carpal tunnel syndrome. The mobile device (mobile phone, smartwatch, tablet computer) 110b preferably comprises an accelerometer 301, a headphone jack 302, a microphone jack 303, a speaker 304, a GPS chipset 305, a Bluetooth component 306, a Wi-Fi component 307, a 3G/4G component 308, a Baseband Processor (for radio control) 309, an applications (or main) processor 310, a JTAG (debugger) 311, a SDRAM memory 312, a Flash memory 313, SIM card 314, LCD display 315, a camera 316, a power management circuit 317 and a battery or power source 318.

Figure 13:
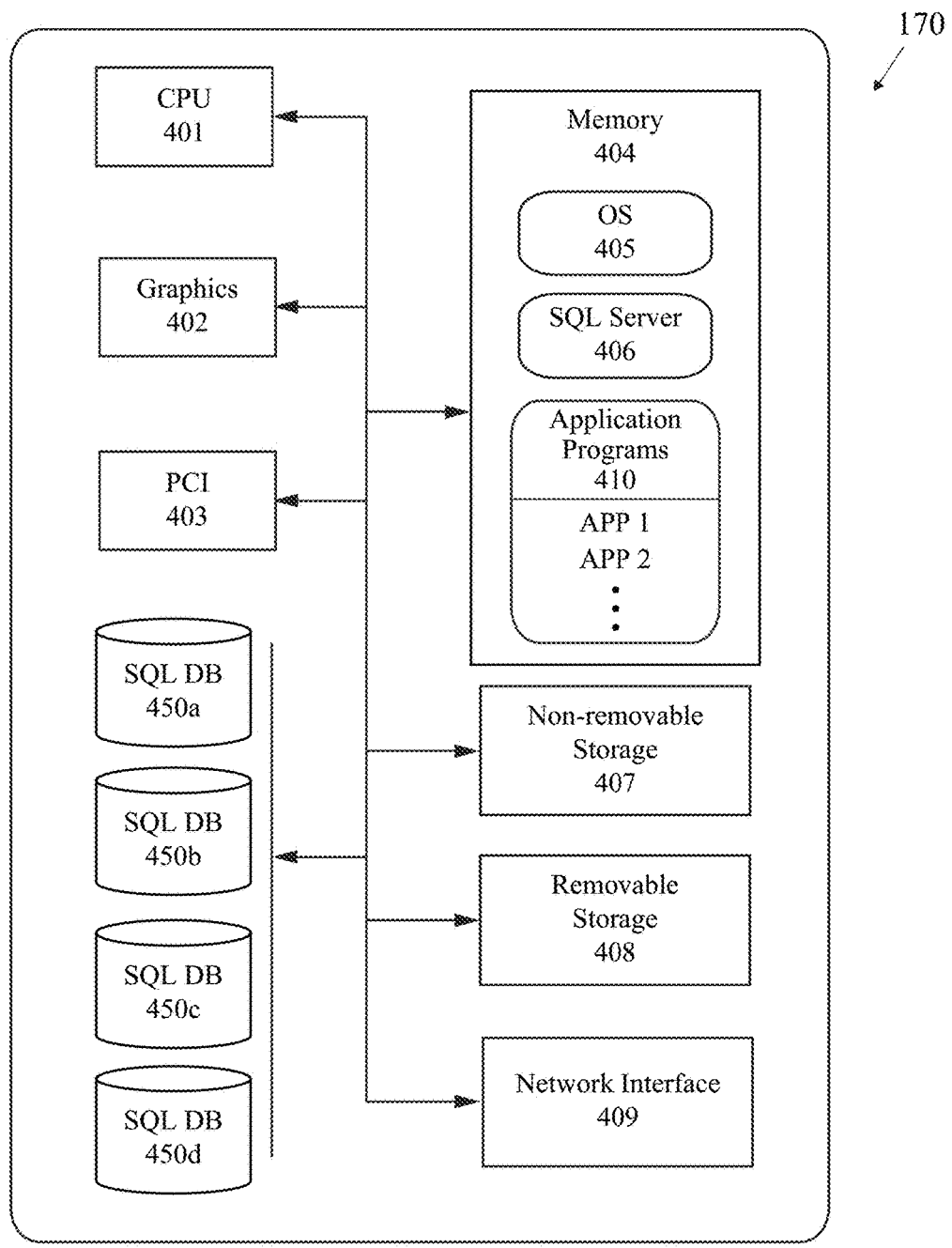
FIG. 13 is a block diagram of a server utilized with a system for monitoring carpal tunnel syndrome.

FIG. 13 is a block diagram of a server 170 utilized with a system for monitoring carpal tunnel syndrome. Components of the server 170 of the system 100 includes a CPU component 401, a graphics component 402, PCI/PCI Express 403, memory 404, non-removable storage 407, removable storage 408, Network Interface 409, including one or more connections to a fixed network, and SQL database(s) 450a-450d, which includes the venue's CRM. Included in the memory 404 is an operating system 405, a SQL server 406 or other database engine, and computer programs/software 410. The server 170 also includes at least one computer program configured to receive data uploads and store the data uploads in the SQL database.

Figure 14:
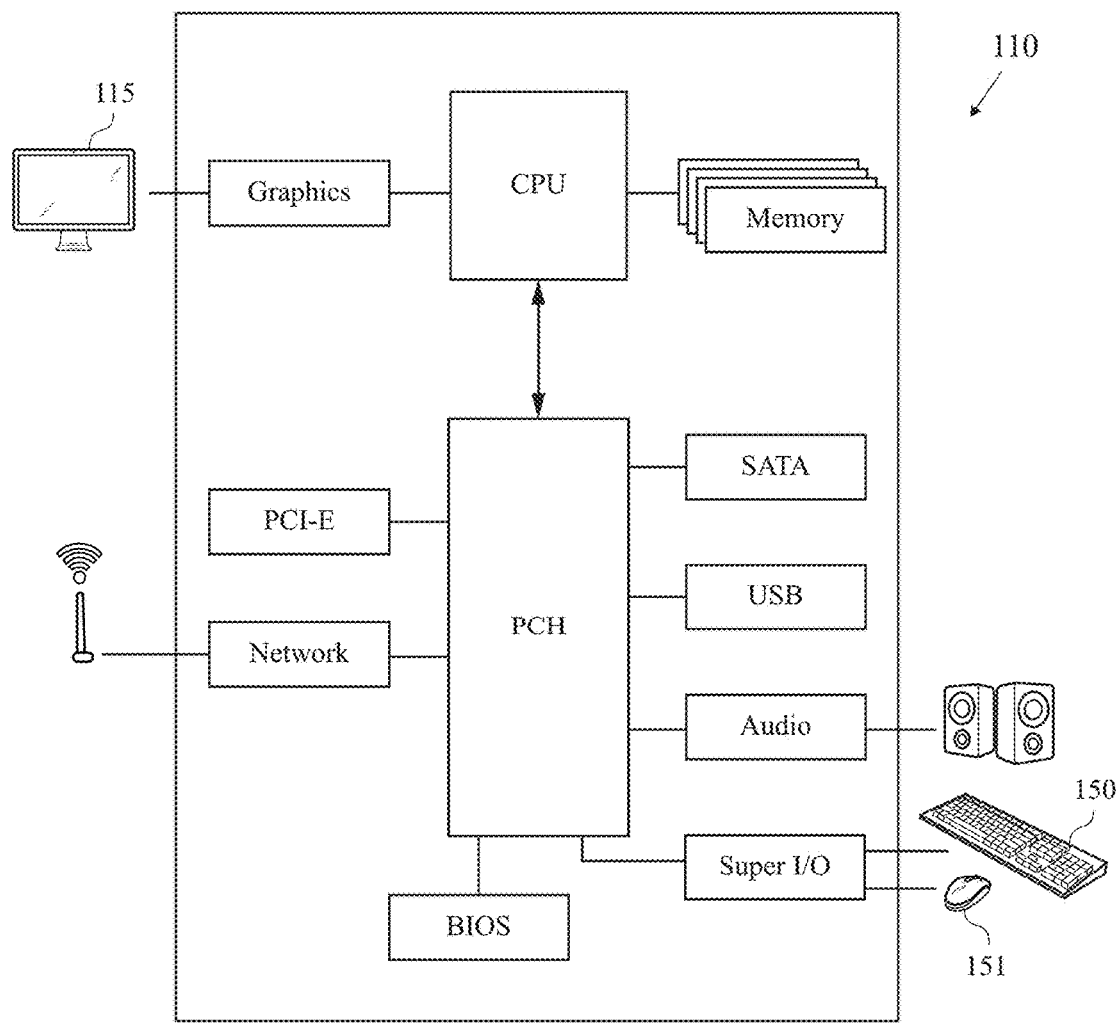
FIG. 14 is a block diagram of a system for monitoring carpal tunnel syndrome.

FIG. 14 is a block diagram of a computer 110 of a system 100 for monitoring carpal tunnel syndrome. The computer 110 has a keyboard 150, a mouse 151 and a display screen 115. The computer 110 also preferably includes a CPU, a graphics module, memory, a PCH, a USB an audio module, a SATA module, a BIOS module, a super I/O module, a network connection, and a PCI-E.

Figure 15A:
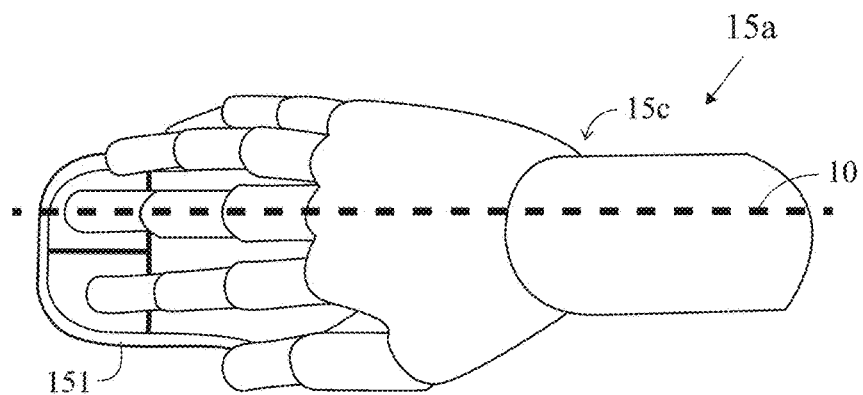
FIG. 15A is an illustration of good carpal use of a mouse by a user.

FIG. 15A illustrates a good carpal use of a mouse 151 by a user wherein the user's hand 15a is at a zero angle 10 relative to the user's wrist 15c.

Figure 15B:
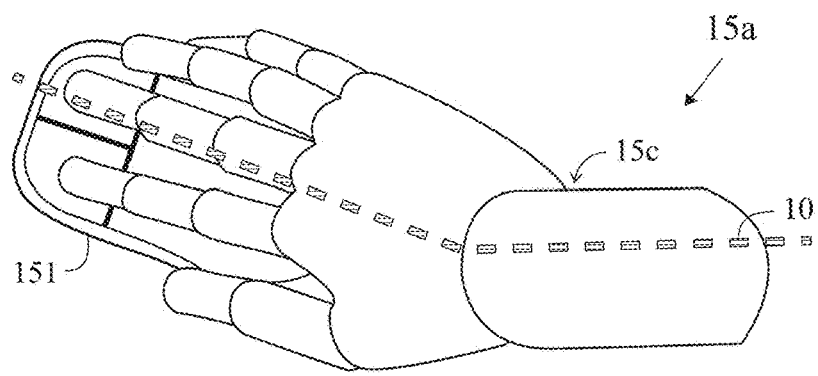
FIG. 15B is an illustration of bad carpal use of a mouse by a user.

FIG. 15B illustrates an angled-hand carpal use of a mouse 151 by a user wherein a user's hand 15a is at an inward angle 10 relative to a user's wrist 15c.

Figure 15C:
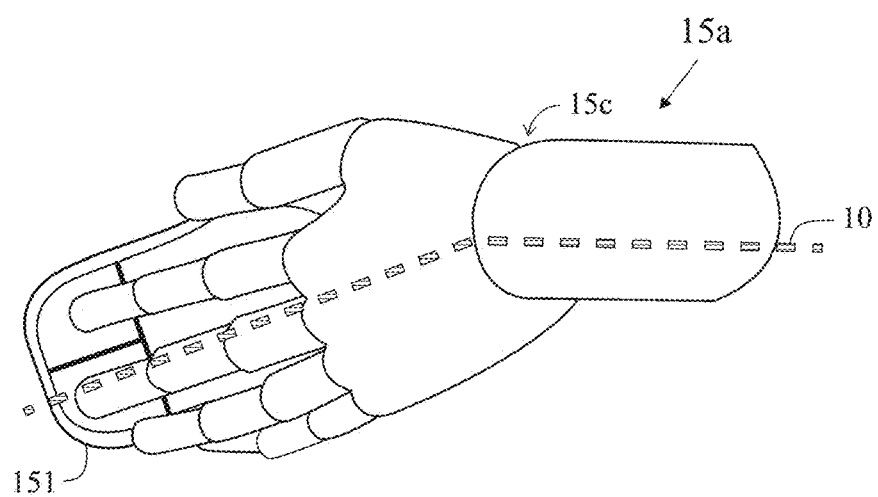
FIG. 15C is an illustration of bad carpal use of a mouse by a user.

FIG. 15C illustrates an angled-hand carpal use of a mouse 151 by a user wherein a user's hand 15a is at an outward angle 10 relative to a user's wrists 15c.

Figure 16A:
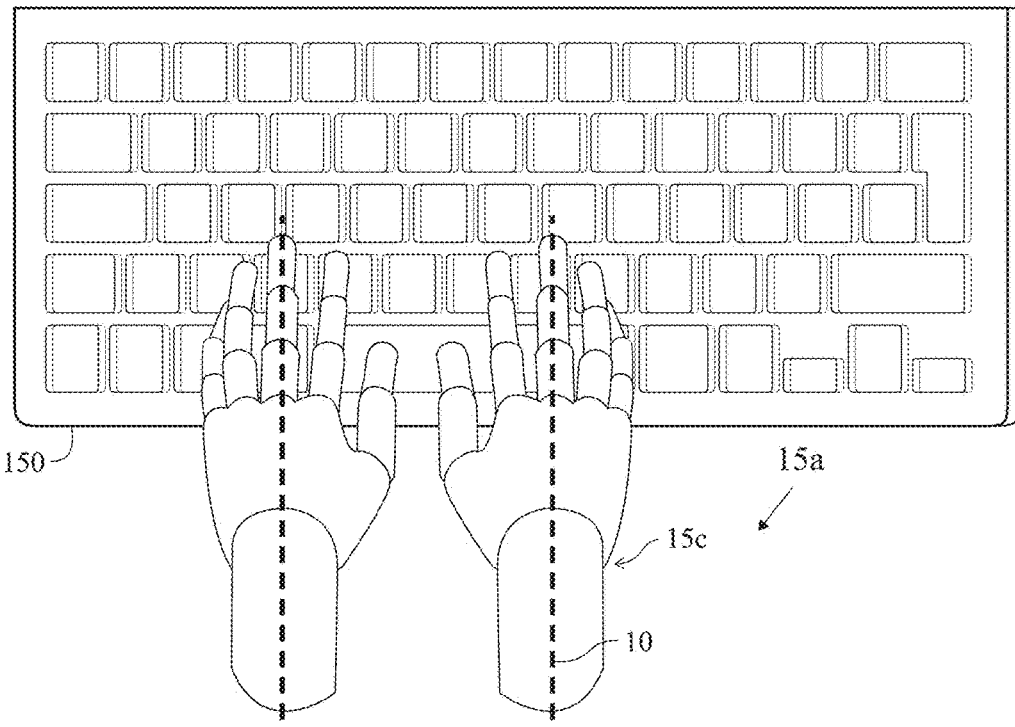
FIG. 16A is an illustration of good carpal use of a keyboard by a user.

FIG. 16A illustrates a good carpal use of a keyboard 150 by a user wherein the user's hands 15a are at a zero angle 10 relative to the user's wrist 15c.

Figure 16B:
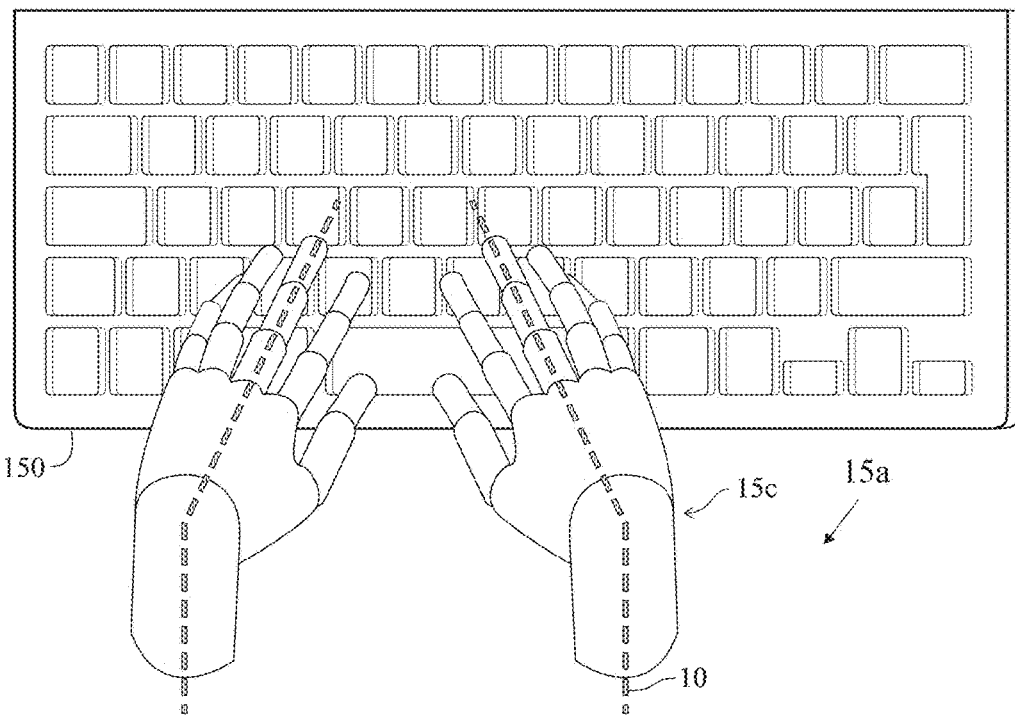
FIG. 16B is an illustration of bad carpal use of a keyboard by a user.

FIG. 16B illustrates an angled-hand carpal use of a keyboard 150 by a user wherein a user's hands 15a are at an inward angle 10 relative to a user's wrists 15c.

Figure 16C:
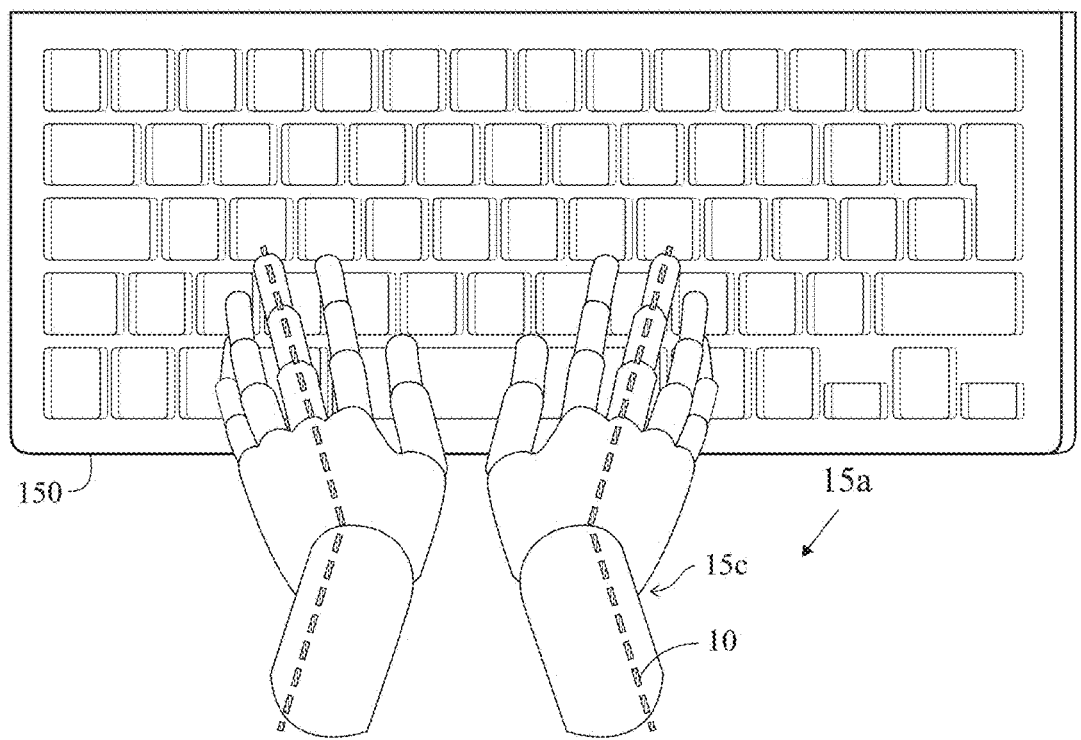
FIG. 16C is an illustration of bad carpal use of a keyboard by a user.

FIG. 16C illustrates an angled-hand carpal use of a keyboard 150 by a user wherein a user's hands 15a are at an outward angle 10 relative to a user's wrists 15c.

Figure 17:
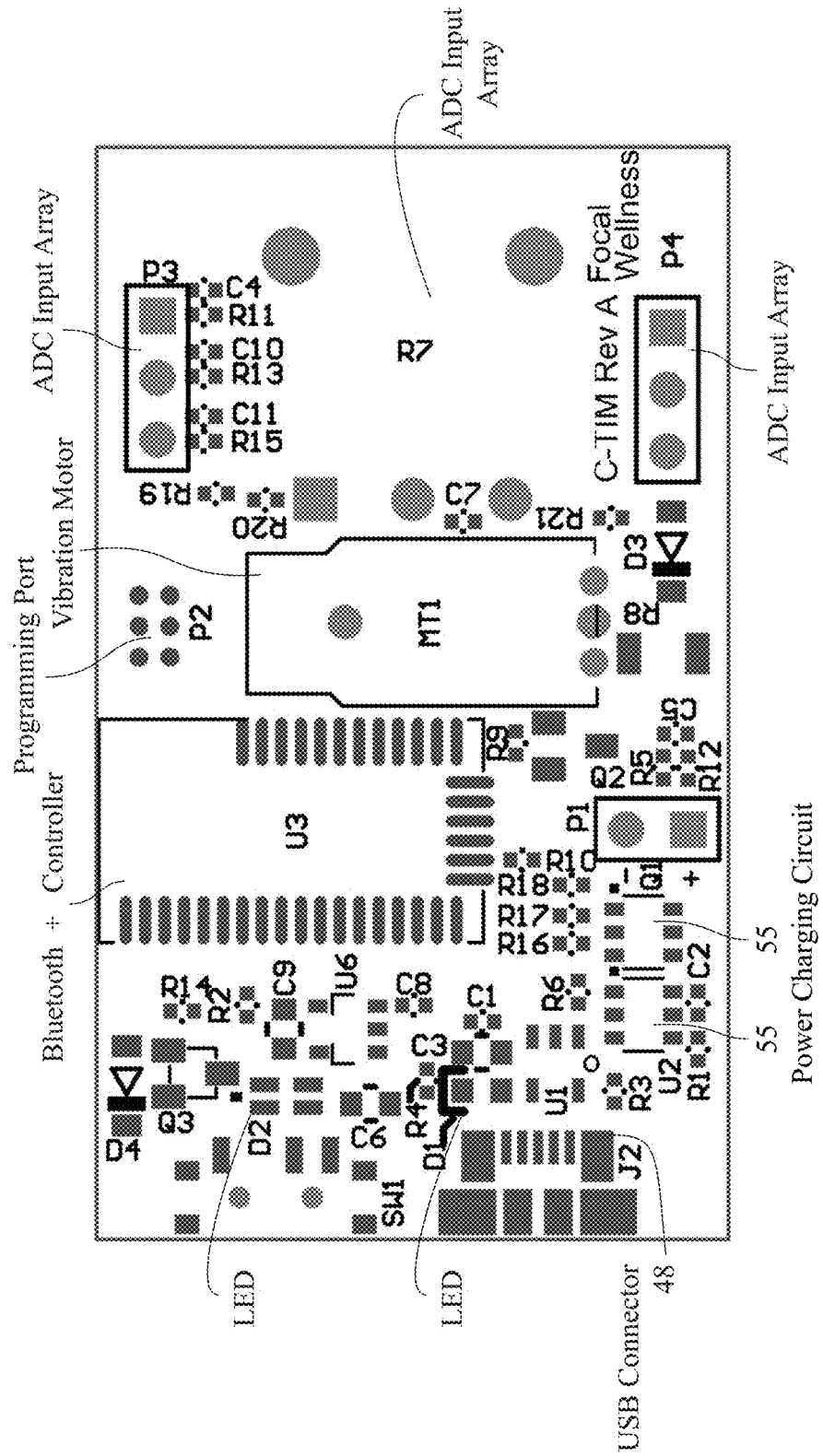
FIG. 17 is a block diagram of circuitry for an alternative embodiment of a device of a system for monitoring carpal tunnel syndrome.

FIG. 17 is a block diagram of circuitry for an alternative embodiment of a device of a system for monitoring carpal tunnel syndrome. This device includes a vibration motor, ADC input arrays, a power charging circuit, a USB connector, LEDs, and a microprocessor with an integrated BLUETOOTH wireless chip.

Figure 18:
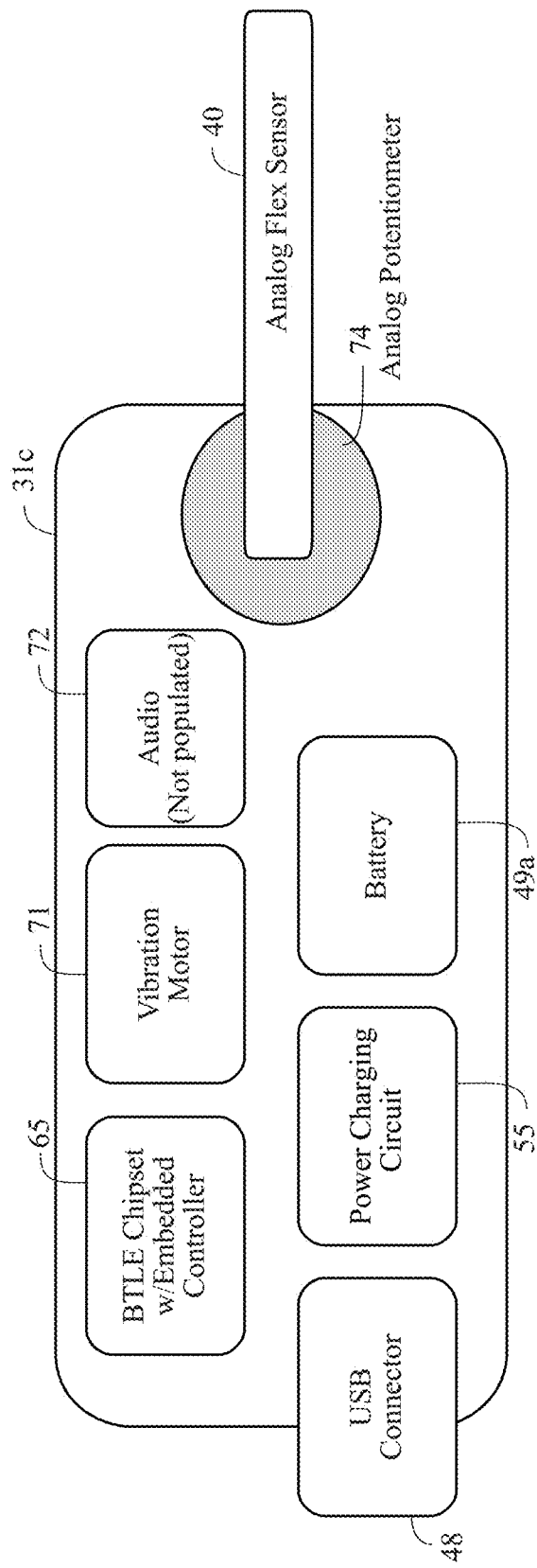
FIG. 18 is a block diagram of an alternative embodiment of a device of a system for monitoring carpal tunnel syndrome.

FIG. 18 is a block diagram of an alternative embodiment of a device of a system for monitoring carpal tunnel syndrome. The circuit board 31c of the device includes a vibration motor 71, an analog flex sensor 40, an analog potentiometer 74, a power charging circuit 55, a USB connector 48, a battery 49a, an audio module 72, and a microprocessor with an integrated BLUETOOTH wireless chip 65.

Figure 19:
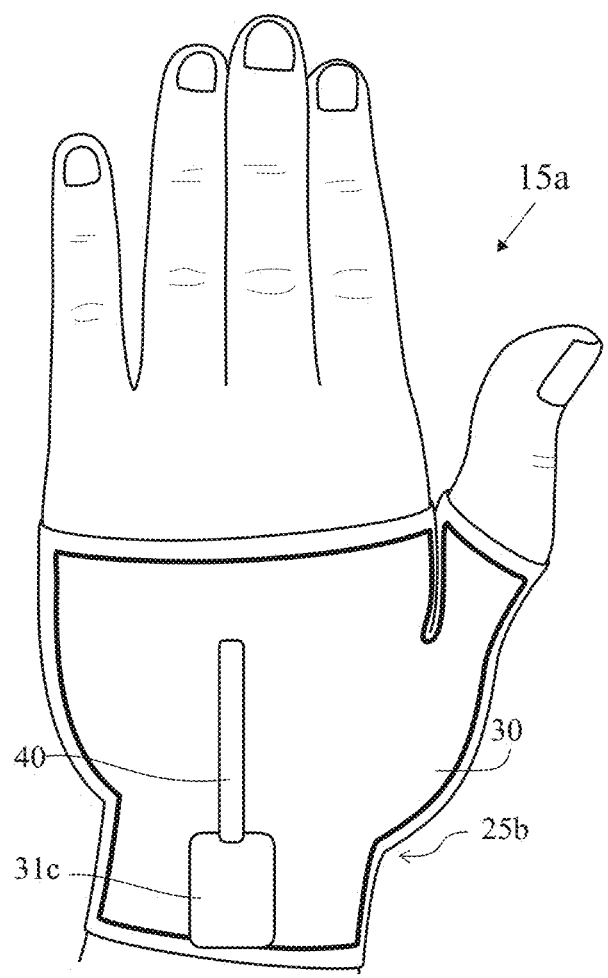
FIG. 19 is an illustration of an alternative embodiment of a device for monitoring carpal tunnel syndrome on a hand of a user.
Figure 19A:
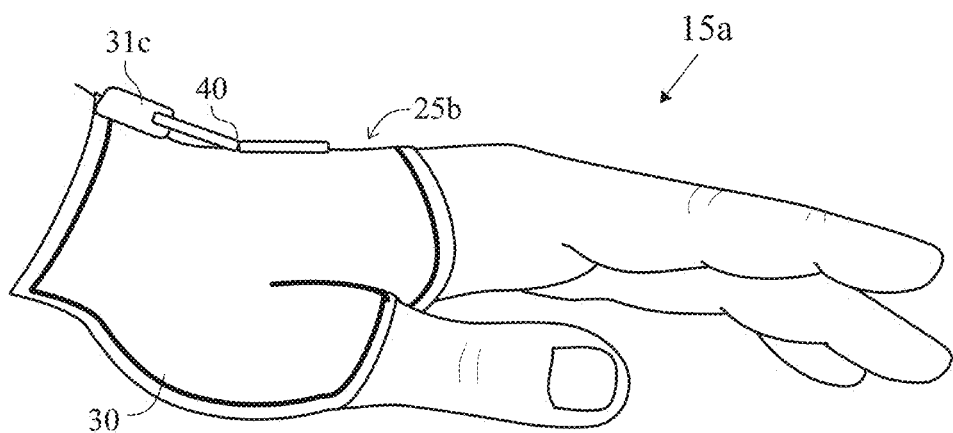
FIG. 19A is an illustration of an alternative embodiment of a device for monitoring carpal tunnel syndrome on a hand of a user.

FIGS. 19 and 19A illustrate an alternative embodiment of a device 25b for monitoring carpal tunnel syndrome on a hand of a user.

Figure 20:
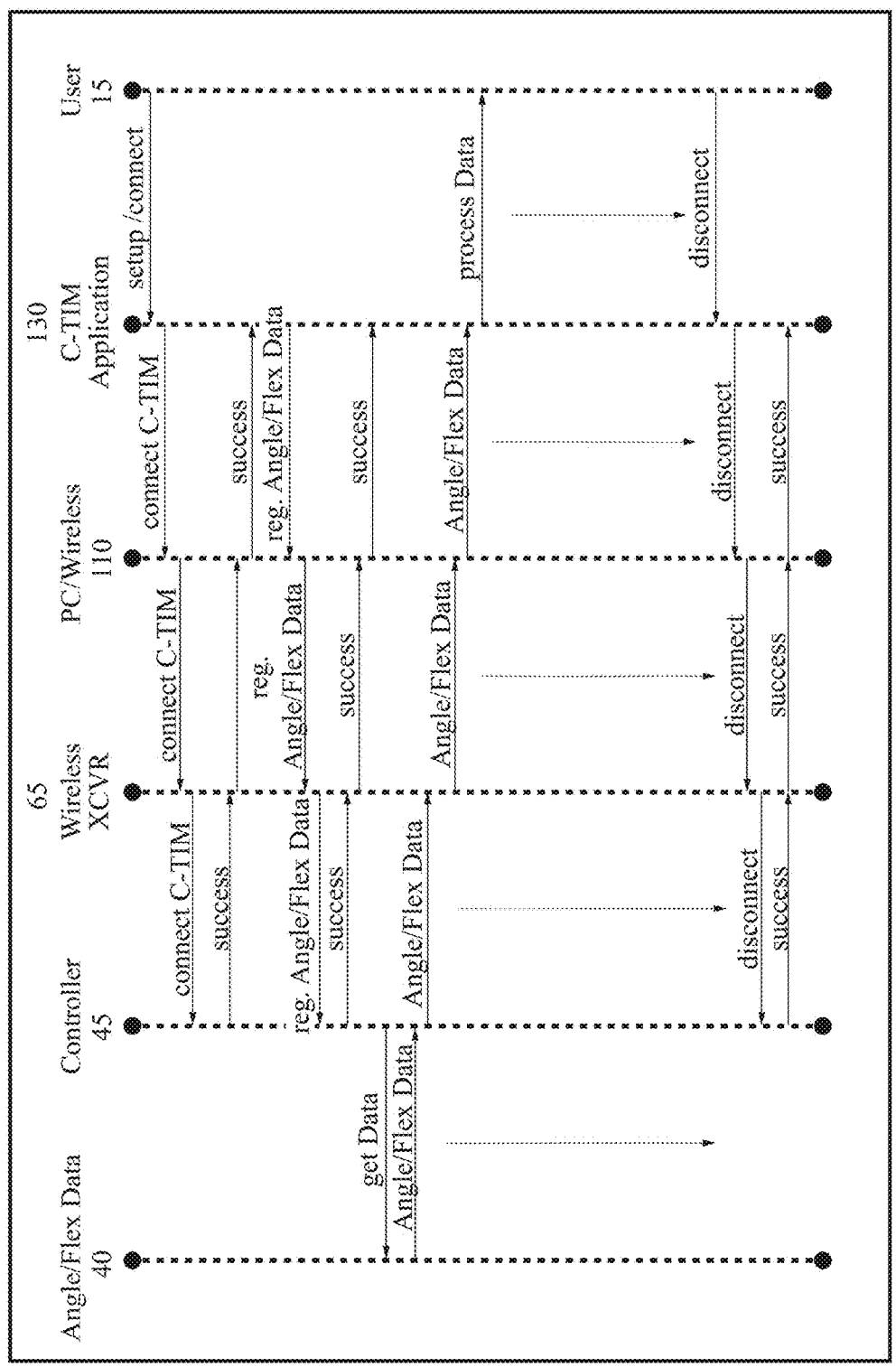
FIG. 20 a communication sequence diagram for an alternative embodiment of a system for monitoring carpal tunnel syndrome.

FIG. 20 a communication sequence diagram 250 for an alternative embodiment of a system for monitoring carpal tunnel syndrome. At an initial stage, the user 15 connects to and sets up the software application 130 running on the computer 110. The software application 130, via a wireless transceiver on the computer 110, connects to the controller 45 of the device 25 through a wireless transceiver 65. The controller 45 confirms the set up with the software application 130. The software application 130 registers angle/flex data with the controller 45. The controller 45 confirms the registration with the software application 130. The controller 45 sends a request for angle/flex data from the angle flex sensor 40. The angle/flex sensor 40 transmits the angle/flex data to the software application 130, and the software application 130 processes the angle/flex data and displays a signal for the user 15. When the user 15 is finished, a disconnect signal is transmitted to the software application 130, which transmits the signal to the controller 45. The controller 45 transmits a success confirmation to the software application 130.

The angle/flex sensor 40 is preferably a FLEXPOINT sensor (FLXT-252-1-001). In operation, as the angle flex sensor 40 bends, the resistance of the sensor 40 changes, with a 180 degrees bend having a resistance as much as two-times a flat resistance of the angle/flex sensor 40. A voltage from the angle/flex sensor 40 is read to monitor the user's hand position when using a mouse or keyboard. If the voltage changes a pre-determined amount, then an alert is transmitted. In a preferred embodiment, a 33 degrees movement of a user's hand up or down, relative a base, good hand position, will result in an alert. Also, a 15 degrees movement of a user's hand to the right or left, relative a base, good hand position, will result in an alert.

Preferably a BGM113 BTLE chipset with a CORTEX M4 processor from Silicon Labs is the combination wireless transceiver and processor chipset utilized with CTS device. Preferably a lithium polymer 80 milliamps power battery is utilized with the CTS device. Preferably a ST Micro FS-L-0095-103-ST IMU sensor is utilized with the CTS device.

Figure 21:
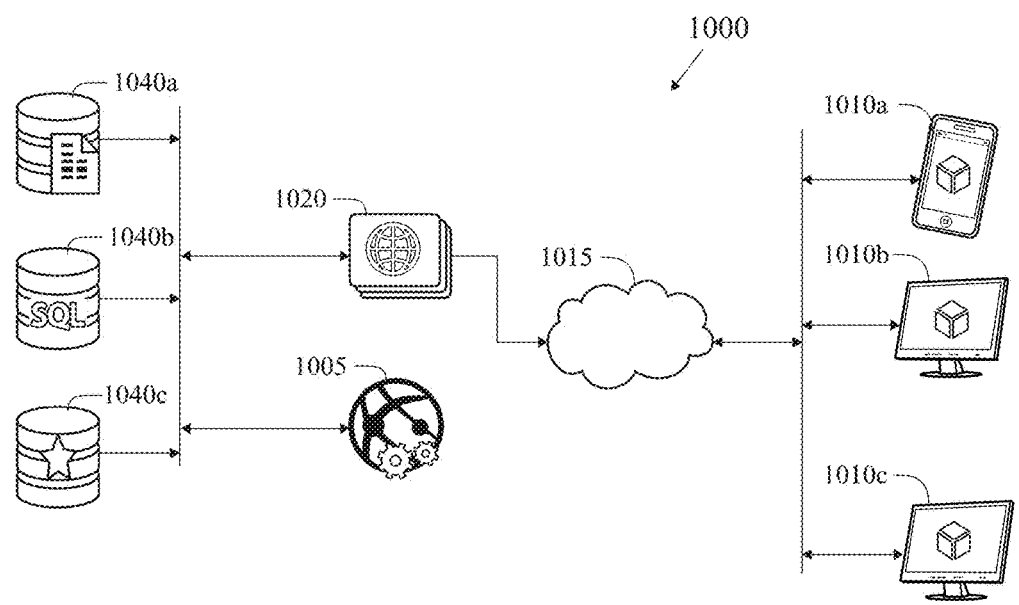
FIG. 21 is a block diagram of a network for monitoring carpal tunnel syndrome.

FIG. 21 is a block diagram of a network 1000 for monitoring carpal tunnel syndrome. Data from mobile phone 1010a, PC 1010b and PC 1010c is sent to the cloud 1015, where files 1020 and transferred to databases 1401a, 1040b and 1040c before being processed at 1005.

Figure 22:
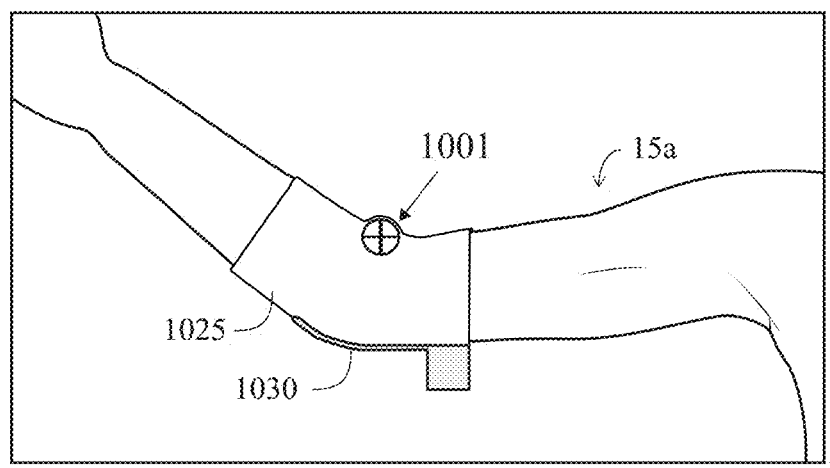
FIG. 22 is an illustration of a monitoring device on an elbow of a user.

FIG. 22 is an illustration of a monitoring device 1025, with a bend sensor 1030 and a target icon 1001 on an elbow 15a of a user.

Figure 23:
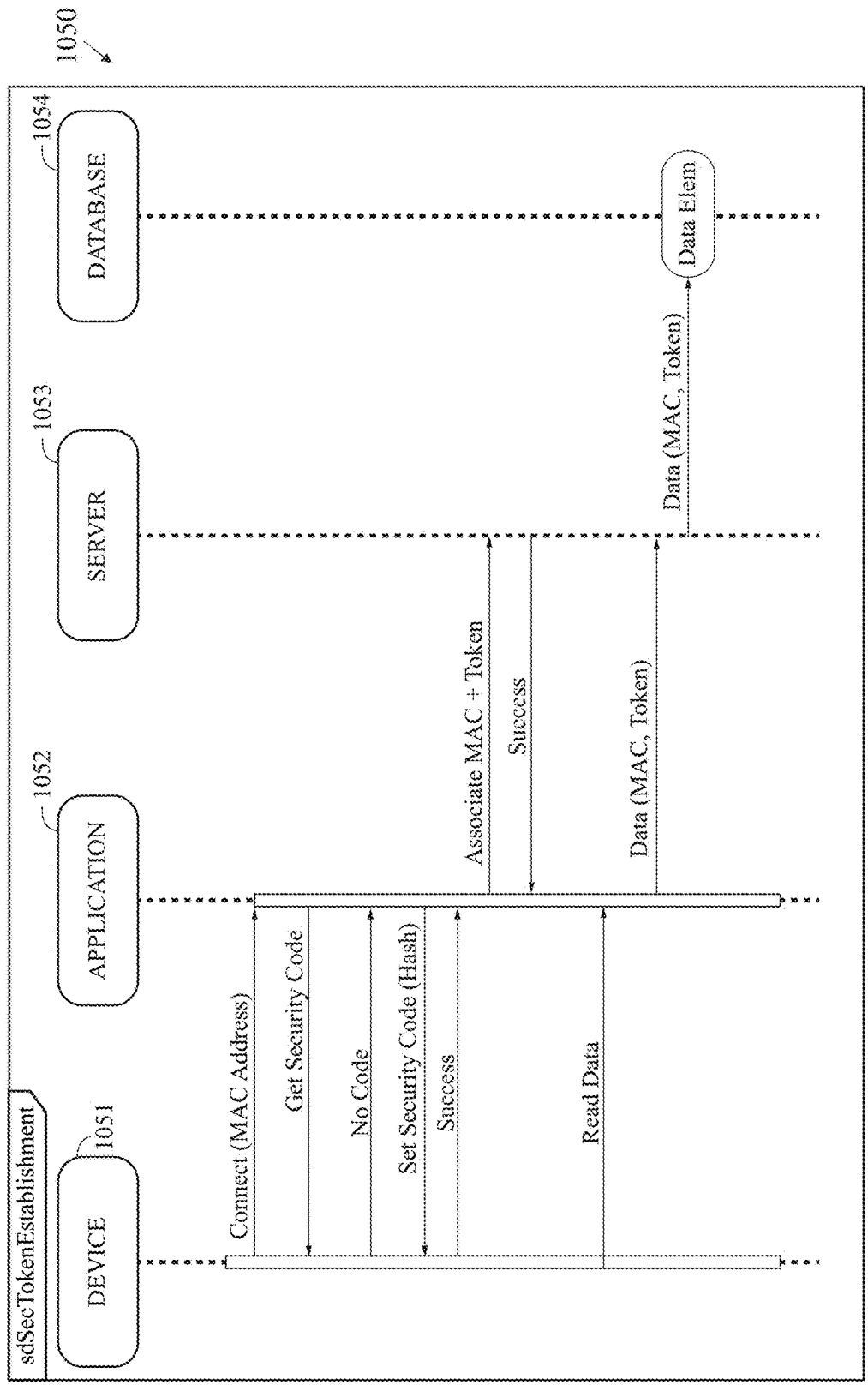
FIG. 23 is a communication sequence diagram for a security protocol for a system for monitoring carpal tunnel syndrome.
Figure 24A:
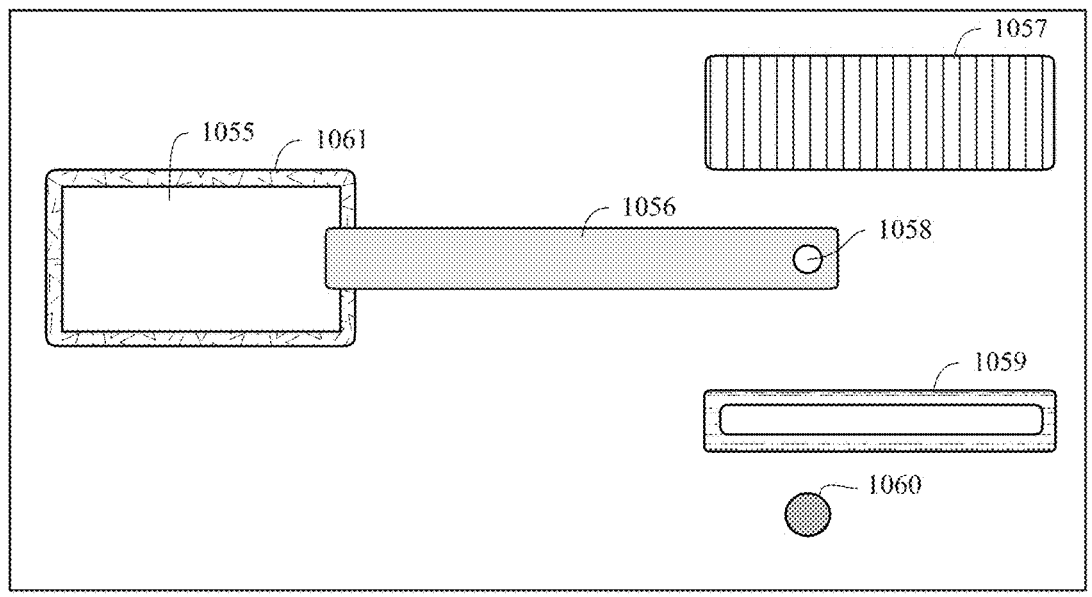
FIG. 24A is an illustration of a sensor.
Figure 24B:
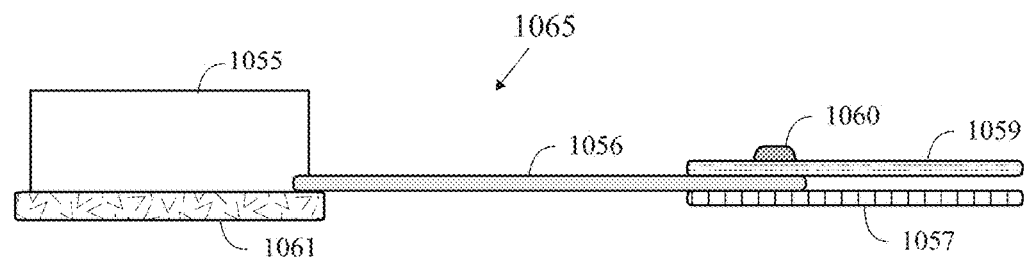
FIG. 24B is an illustration of a sensor.

FIG. 23 is a communication sequence diagram 1050 for a security protocol for a system for monitoring carpal tunnel syndrome showing communications between a device 1051, an application 1052, a server 1053, and a database 1054.

Figure 25A:
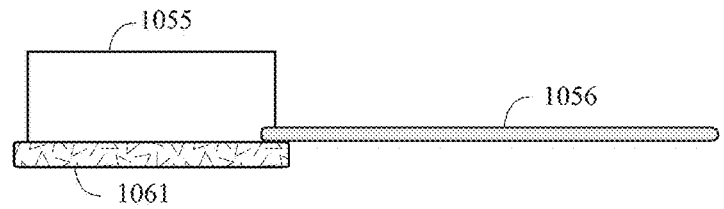
FIG. 25A is an illustration of a sensor.
Figure 25B:
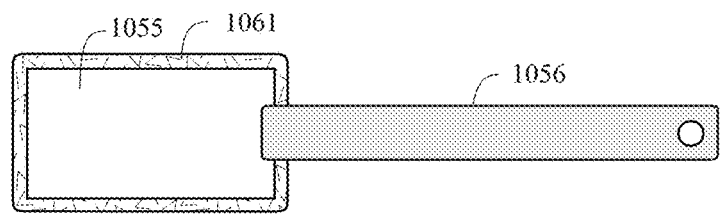
FIG. 25B is an illustration of a sensor.
Figure 25C:
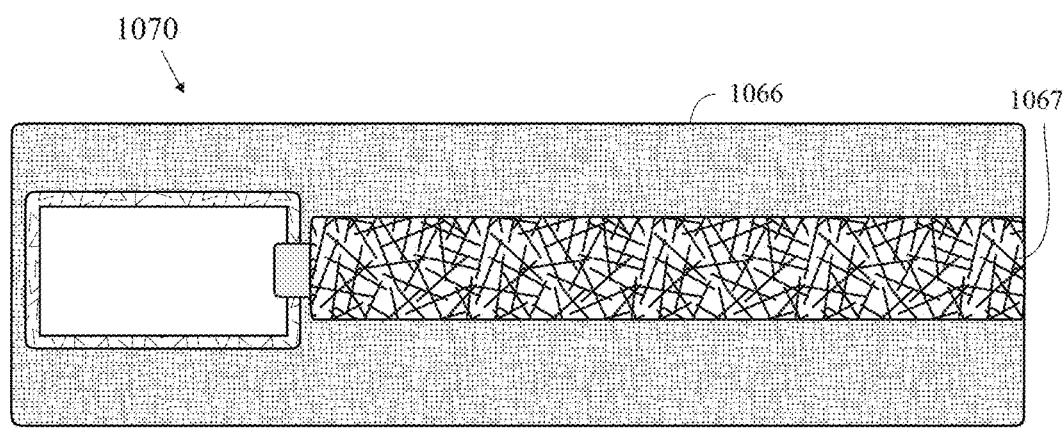
FIG. 25C is an illustration of a sensor.
Figure 25D:
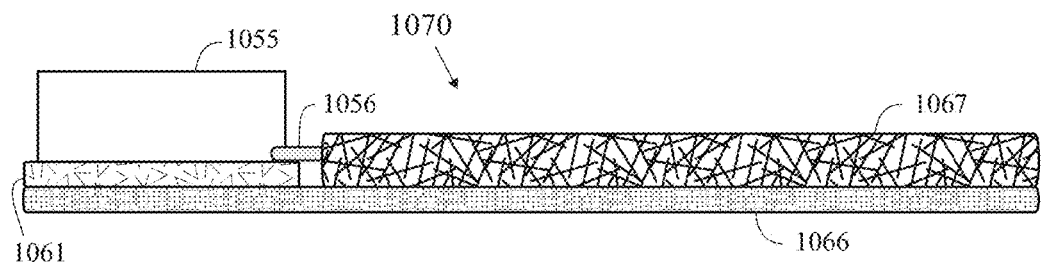
FIG. 25D is an illustration of a sensor.

FIGS. 24A, 24B, 25A, 25B, 25C, and 25D are illustrations of a mechanical alignment sensor 1065 having a computing board 1055, a sensor 1056, an alignment hole 1058, and optional glide plane 1057, an alignment channel 1059, an alignment cap 1060, a fabric clip 1061, a sleeve fabric 1066, and a fabric channel 1067. A whole assembly 1070 is shown in FIG. 25D.

Figure 26:
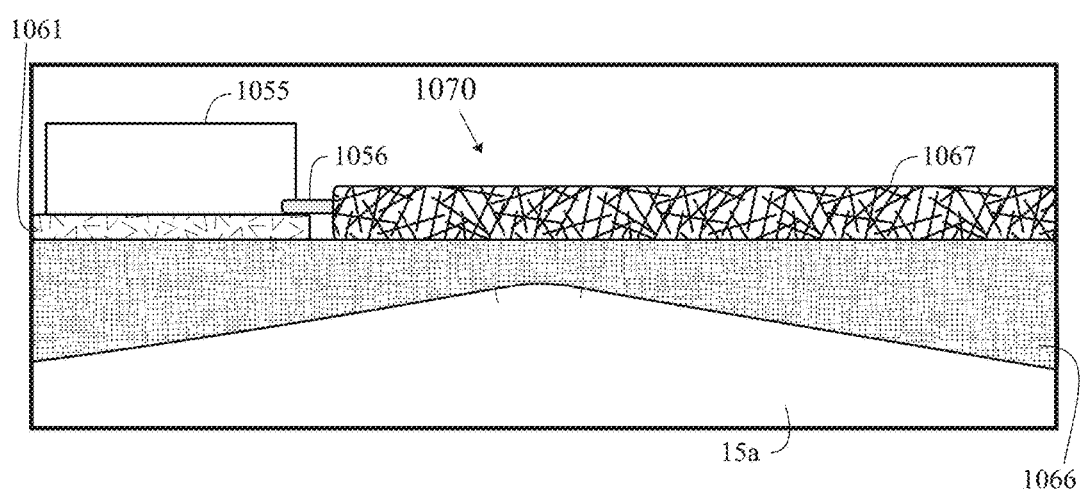
FIG. 26 is a block diagram of cubital tunnel sleeve device.
Figure 29:
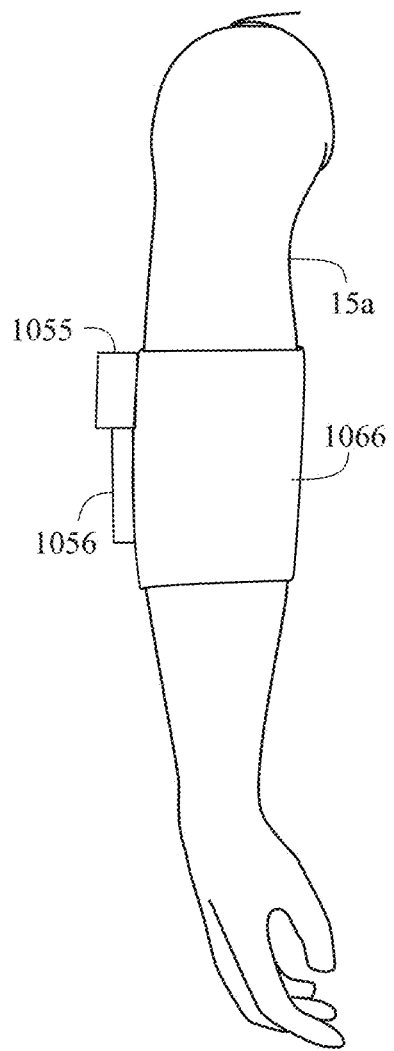
FIG. 29 is an illustration of a cubital tunnel sleeve device on an elbow of a user.

A cubital tunnel sleeve device 1070 is shown in FIG. 26, and it includes a computing board 1055, a sensor 1056, a fabric channel 1067, a fabric clip 1061, a sleeve fabric 1066 for padding on a user's elbow 15a as shown in FIG. 29.

Figure 28A:
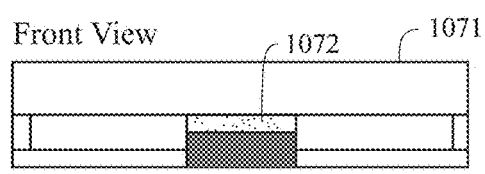
FIG. 28A is an illustration of a sensor gap.
Figure 28B:
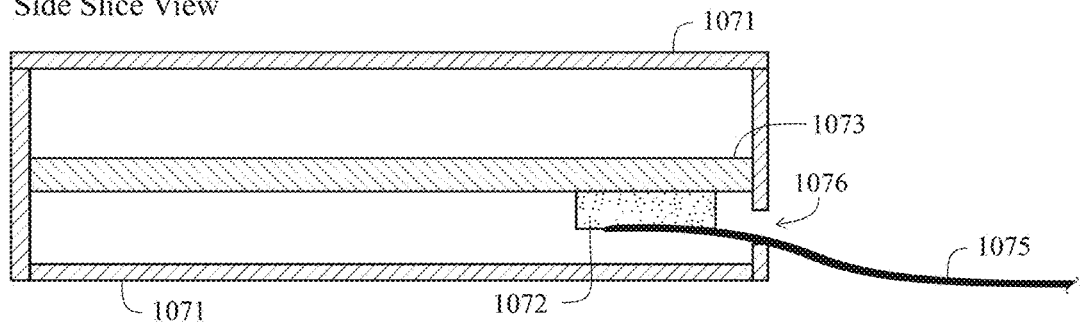
FIG. 28B is an illustration of a sensor gap.

FIGS. 28A and 28B are illustrations of a sensor gap. A sensor housing 1071 has a pot wheel 1072, a PCB 1073, a bend sensor 1075 and an opening of a housing 1076.

Figure 27:
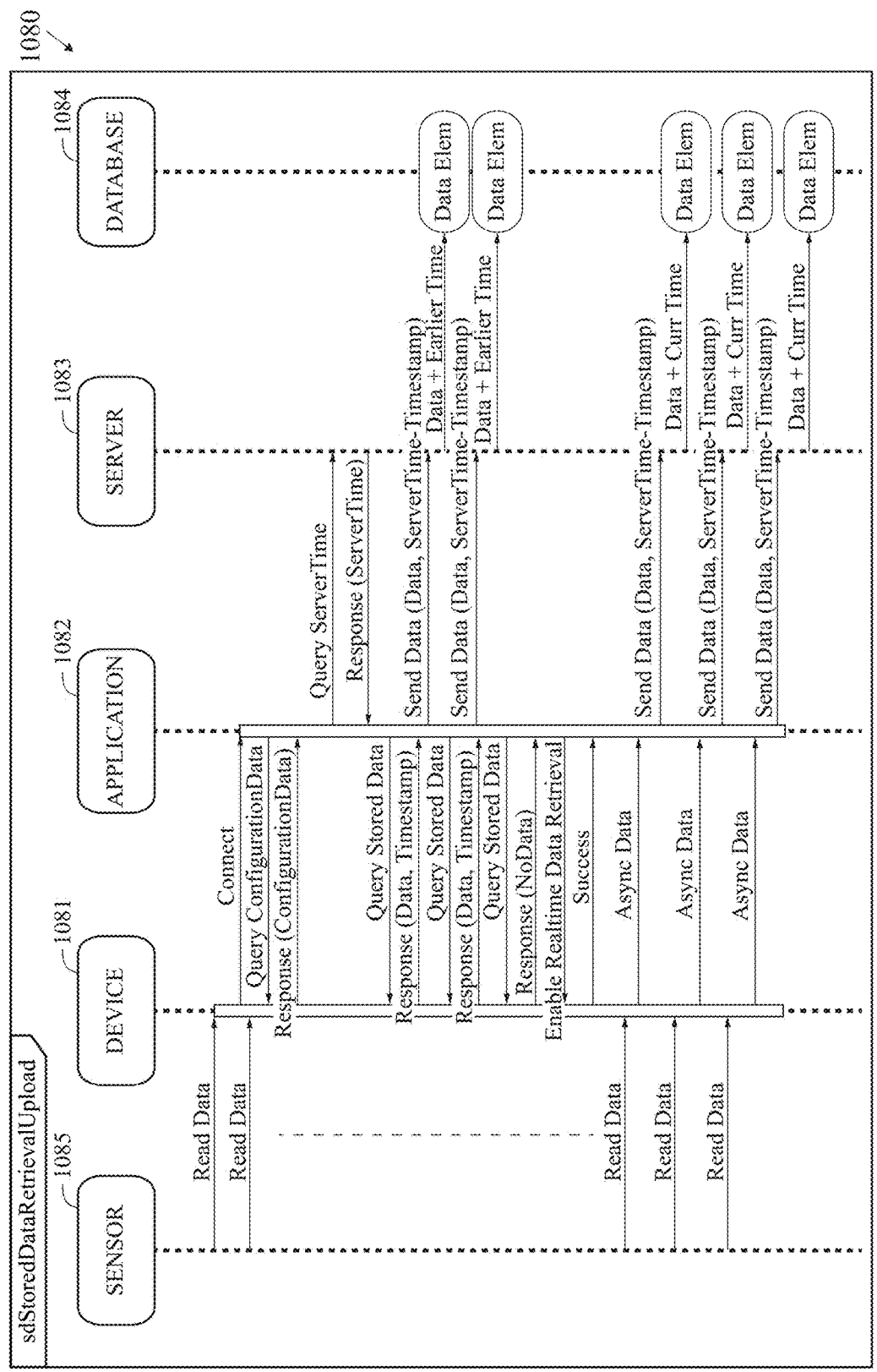
FIG. 27 is a communication sequence diagram for a data upload for a system for monitoring carpal tunnel syndrome.

FIG. 27 is a communication sequence diagram 1080 for a data upload for a system for monitoring carpal tunnel syndrome showing communications between a sensor 1085, a device 1081, an application 1082, a server 1083, and a database 1084.

Figure 30:
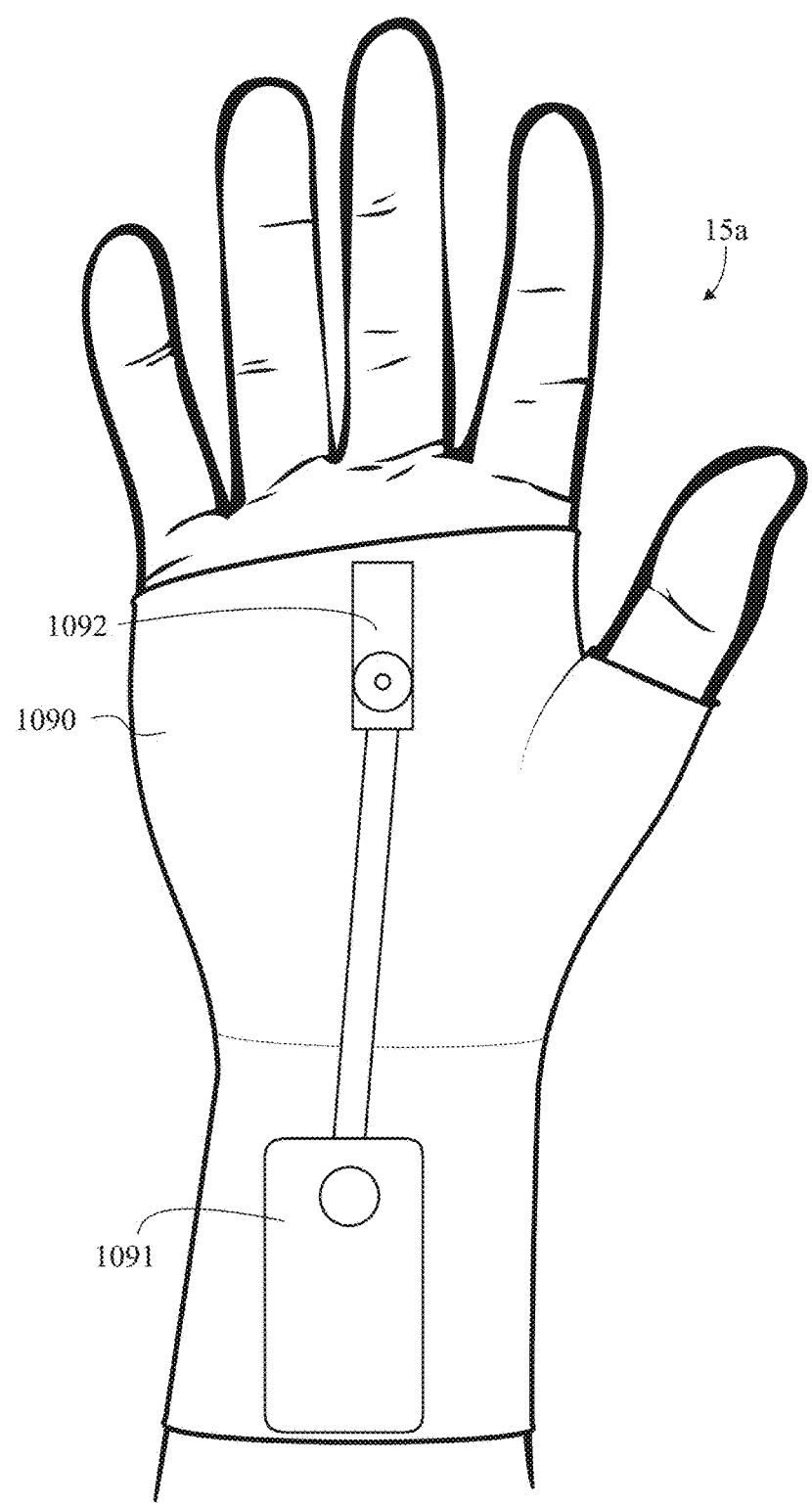
FIG. 30 is an illustration of a C-TIM on a hand of a user.

FIG. 30 shows a C-TIM 1090 on a hand 15a of a user. The C-TIM 1090, in the form of a glove, has a sensor 1092 and a computing board 1091.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim as my invention the following:

1. A device for monitoring Cubital tunnel syndrome ("CuTS"), the device comprising:
   a body configured to be worn on an arm of a user;
   a plurality of sensors;
   a processor positioned within the body and in communication with the plurality of sensors;
   a vibration mechanism positioned within the body and in communication with the processor; and
   a power source positioned within the body and in communication with the processor;
   wherein the plurality of sensors monitors a position of the user's upper arm and forearm to prevent CuTS wherein a resistance of the plurality of sensors changes when the user's elbow is bent;
   wherein a voltage from the plurality of sensors is monitored by the processor;
   wherein the processor of the article is configured to determine if the user's upper arm and forearm are in a CuTS position and the processor is configured to activate an alert signal when a pre-determined change in the value of the voltage from the plurality of sensors is sent to the processor to alert the user to the CuTS position.

2. The device according to claim 1 wherein the plurality of sensors is a plurality of inertia measurement units (IMU), which includes: accelerometer, gyroscope and magnetometer capabilities.

3. The device according to claim 1 wherein the plurality of sensors is a plurality of piezo electric sensors.

4. The device according to claim 2 further comprising a plurality of LEDs for indication of proper arm position.

5. The device according to claim 1 further comprising a plurality of LEDs for indication of proper arm position.

6. The system according to claim 1 wherein the vibration mechanism indicates an arm position.

7. The device of claim 1 wherein the device is a sleeve worn around the elbow.

8. The device of claim 1 wherein the device is affixed directly to the skin.

9. A system for monitoring cubital tunnel syndrome ("CuTS") according to claim 1 further comprising:
   a computing device comprising
      a display screen,
      a processor,
      a wireless transceiver, and
      a software application;
   wherein the alert signal is received at the wireless transceiver of the computer and the application is configured to display a warning on the display screen to alert the user to the CuTS position.

10. The system of claim 9 wherein the alert signal is an audio alert, a visual alert, or the vibration mechanism being executed on the device.

11. The system of claim 9 wherein the alert signal can be configured by the user for different environments.

12. A device for monitoring Cubital tunnel syndrome ("CuTS"), the device comprising:
   a body configured to be worn on an arm of a user;
   a sensor;
   a processor positioned within the body and in communication with the sensor;
   a vibration mechanism positioned within the body and in communication with the processor; and
   a power source positioned within the body and in communication with the processor;
   wherein the sensor monitors a position of the user's upper arm and forearm to prevent CuTS wherein a resistance of the sensor changes when the user's elbow is bent;
   wherein a voltage from the sensor is monitored by the processor;
   wherein the processor of the article is configured to determine if the user's upper arm and forearm are in a CuTS position and the processor is configured to activate an alert signal when a pre-determined change in the value of the voltage from the sensor is sent to the processor to alert the user to the CuTS position.

* * * * *